United States Patent
Attia-Vigneau et al.

(10) Patent No.: US 12,083,157 B2
(45) Date of Patent: Sep. 10, 2024

(54) USE OF POLYLYSINE DENDRIMERS IN THE PREVENTION AND MANAGEMENT OF ACNE-PRONE SKIN AND ACNEIC SKIN

(71) Applicant: Lucas Meyer Cosmetics, Massy (FR)

(72) Inventors: Joan Attia-Vigneau, Saint Clar De Riviere (FR); Estelle Loing, Quebec (CA); Magali Borel, Paris (FR)

(73) Assignee: LUCAS MEYER COSMETICS, Massy (FR)

( * ) Notice: Subject to any disclaimer, the term of this patent is extended or adjusted under 35 U.S.C. 154(b) by 136 days.

(21) Appl. No.: 17/441,482

(22) PCT Filed: Feb. 21, 2020

(86) PCT No.: PCT/US2020/019173
§ 371 (c)(1),
(2) Date: Sep. 21, 2021

(87) PCT Pub. No.: WO2020/197669
PCT Pub. Date: Oct. 1, 2020

(65) Prior Publication Data
US 2022/0152147 A1 May 19, 2022

Related U.S. Application Data

(60) Provisional application No. 62/823,730, filed on Mar. 26, 2019.

(51) Int. Cl.
| | |
|---|---|
| *A61K 38/16* | (2006.01) |
| *A61K 8/362* | (2006.01) |
| *A61K 8/365* | (2006.01) |
| *A61K 8/64* | (2006.01) |
| *A61K 8/67* | (2006.01) |
| *A61P 17/10* | (2006.01) |
| *A61Q 17/00* | (2006.01) |
| *A61Q 19/00* | (2006.01) |

(52) U.S. Cl.
CPC .............. *A61K 38/16* (2013.01); *A61K 8/362* (2013.01); *A61K 8/365* (2013.01); *A61K 8/64* (2013.01); *A61K 8/671* (2013.01); *A61P 17/10* (2018.01); *A61Q 17/005* (2013.01); *A61K 2800/5426* (2013.01); *A61K 2800/544* (2013.01)

(58) Field of Classification Search
CPC ........ A61K 38/16; A61K 8/362; A61K 8/365; A61K 8/64; A61K 8/671; A61K 2800/5426; A61K 2800/544; A61K 8/88; A61P 17/10; A61P 17/005; A61Q 19/00; A61Q 19/008
See application file for complete search history.

(56) References Cited

U.S. PATENT DOCUMENTS

| | | | |
|---|---|---|---|
| 4,289,872 | A | 9/1981 | Denkewalter et al. |
| 6,001,342 | A | 12/1999 | Forestier et al. |
| 9,855,223 | B2 | 1/2018 | Chauhan et al. |
| 2010/0324146 | A1 | 12/2010 | Fairley |
| 2016/0206572 | A1 | 7/2016 | Chauhan et al. |
| 2018/0256480 | A1 | 9/2018 | Deng et al. |

FOREIGN PATENT DOCUMENTS

| | | |
|---|---|---|
| CN | 108743452 | 11/2018 |
| EP | 0 696 451 | 2/1996 |

OTHER PUBLICATIONS

Dong, H.-X et al. "Synthesis of Poly-L-lysine Dendrimers" *Synthetic Materials Aging and Application*, 2010, pp. 8-11, abstract only.
Written Opinion in International Application No. PCT/US2020/019173, May 25, 2020, pp. 1-11.
Klok, H.-A et al. "Dendritic-Graft Polypeptides" *Macromolecules*, Nov. 5, 2002, pp. 8718-8723, vol. 35, No. 23, XP-002250744.
Teertstra, S. J. et al. "Dendrigraft polymers: macromolecular engineering on a mesoscopic scale" *Progress in Polymer Science*, Apr. 1, 2004, pp. 277-327, vol. 29, No. 4.
Rodriguez-Hernandez, J. et al. "Highly Branched Poly(L-lysine)" *Biomacromolecules*, Mar. 1, 2003, pp. 249-258, vol. 4, No. 2, XP-002250742.
Mirakabad, F. S. T. et al. "Peptide dendrimers as valuable biomaterials in medical sciences" *Life Sciences*, available online Aug. 12, 2019, pp. 1-12, vol. 233.

*Primary Examiner* — Julie Ha
(74) *Attorney, Agent, or Firm* — SALIWANCHIK, LLOYD & EISENSCHENK

(57) ABSTRACT

A method for treating acne vulgaris by administering a polylysine dendrimer or a salt thereof. Methods for the management of blemish- or acne-prone skin are also described. The polylysine dendrimer is used as an active for restoring or rebalancing skin microbiota. The polylysine dendrimer is also used as an active agent for improving or restoring the aspect and the feel of the skin to be treated.

14 Claims, 7 Drawing Sheets

USE OF POLYLYSINE DENDRIMERS IN THE PREVENTION AND MANAGEMENT OF ACNE-PRONE SKIN AND ACNEIC SKIN

BACKGROUND

Acne vulgaris, also known simply as acne, is a common, chronic, inflammatory disease of the glands that produce sebum (sebaceous follicles). Acne results in the formation of inflamed elevations (papules, pustules, nodules, and cysts), comedones (blackheads and whiteheads), and scars on the skin. Acne is one of the most common disorders treated by dermatologists and other healthcare providers. More than 90% of world population is affected by acne at some point in their life. The pathogenesis of acne is multifactorial and involves four key factors with interrelated mechanisms: increased sebum production, hyperkeratinization, skin inflammation, and *Cutibacterium acnes* proliferation.

*Cutibacterium acnes* (formerly *Propionibacterium acnes*) is ubiquitously present in human sebaceous follicles of the skin, with a predominance on the face and the back. *C. acnes* is a prevalent member of normal skin microbiota and plays an important role in the maintenance of normal cutaneous microbiota by inhibiting the development of some pathogenic bacteria such as *Staphylococcus aureus* and by maintaining acidic pH acid in pilosebaceous follicles, Although *C. acnes* is commensal, it is generally considered as being involved in the pathogenesis of acne by promoting inflammation. Indeed, a number of studies showed that, in the skin, *C. acnes* activates innate immunity via Toll-like receptors expressed by monocytes and keratinocytes and increases the secretion of interleukins. Besides, *C. acnes* was shown to be associated with opportunistic infections, especially in the context of indwelling medical device. Its dual role in skin microbiota balance, acne inflammatory conditions and opportunistic infections led to the assumption that certain strains of *C. acnes* might be characterized by an elevated pathogenic and inflammatory potentials.

Phylogenetic studies provided valuable insights into the genetic population structure of *C. acnes*. It was shown that *C. acnes* has an overall clonal structure, and its isolates can be classified into a number of statistically significant clades or phylogroups designated types IA1, IA2, IB, IC, II, and III. The phylogroups were shown to display differences in their associations with specific types of infections and vary in their production of putative virulence determinants, inflammatory potential, antibiotic resistances, aggregative properties, and morphological features. Phylotypes IA1, IA2, IB, IC of *C. acnes* have been identified as acneic strains while phylotypes II and III are classified as non-acneic strains. Phylotype IA1 was shown to be the most abundant strains in acneic strains while phylotypes II and III are mostly present in healthy, non-acneic, skins.

Indeed, a number of independent epidemiological studies showed a correlation between clonal complexes from the type IA1 phylogroup and moderate-to-severe acne (Scholz et al., PlosOne, 2014, e104199, Barnard et al. Journal of Clinical Microbiology, 2015, 53, 1149-1155).

Recently, Dagnelie et al. (Acta Derm Venereol, 2018; 98:262-267) determined and compared the different phylotypes, clonal complexes (CC) and single-locus sequence typing (SLST) types in patients with severe acne versus healthy patients. They showed that healthy patients carried phylotypes IA1 (39.1%) and II (43.4%), whereas the acne group carried a high predominance of IA1 (84.4%), especially on the back (95.6%): IA1 SLST-type was significantly associated with severe acne. Of note, Dagnelie et al. reported that inflammatory severe acne of both face and back is associated with a significant loss in *C. acnes* diversity population. Because microbiota modulated the innate immunity of the skin, it is believed that such a loss of diversity could trigger inflammation and promote inflammatory acne lesions. In a very recent publication, Dagnelie et al. provided evidence that a loss in *C. acnes* subgroups diversity on the sin does trigger the innate immune system activation and thus the development of cutaneous inflammation (Dagnelie et al., JEADV, 2019; 33:2340-2348). As of today, there are several lines of treatment to manage acne depending on its severity. The treatments are essentially based on two types of active ingredients: topical retinoids which exert anti-inflammatory action, normalize skin desquamation and exert comedolytic action, and antibiotics and bactericides such as benzoyl peroxide which are used for reducing the overall presence of *C. acnes* on the skin. The treatment of moderate and severe acne generally combines topical combination therapy with benzyl peroxide and retinoids or antibiotics. Oral treatments with antibiotics and isotretinoin can also be prescribed. In women, combined oral pill can be also prescribed. Unfortunately, these treatments have also several drawbacks such as skin irritation, dermatitis or photosensitivity. The use of antibiotics is also controversial due to antibiotics resistance issue and can lead to microbiota unbalance.

However, none of these treatments aims to rebalance skin microbiota so as to promote non-acneic *C. acnes* strains as compared to acneic *C. acnes* strains.

There is thus a need for alternative methods to manage acneic skin as well acneic-prone skin and blemish-prone skin.

SUMMARY OF THE INVENTION

The invention relates to the cosmetic, non-therapeutic use of a polylysine dendrimer or a salt thereof as an active ingredient in the management of acne-prone skin and blemish-prone skin. The invention also relates to the use of a polylysine dendrimer or a salt thereof as an active ingredient for treating or preventing acne vulgaris.

In some embodiments, the polylysine dendrimer or a salt thereof is used as an active ingredient for restoring or rebalancing skin microbiota, preferably restoring *C. acnes* diversity on the skin. For instance, the polylysine dendrimer or a salt thereof may be used as an active ingredient for decreasing the abundance of acneic *C. acnes* strains, preferably *C. acnes* strains belonging to phylotypes IA1, IA2, IB and IC, more preferably to phylotype IA1 on the skin. Alternatively or additionally, the polylysine dendrimer or a salt thereof may be used for increasing the abundance of non-acneic *C. acnes* strains, preferably *C. acnes* strains belonging to phylotypes II or III, preferably phylotype II, on the skin.

In some embodiments, the polylysine dendrimer or a salt thereof is used as an active ingredient for:
- improving skin aspect and feel, and/or
- restoring skin comfort and/or
- preventing, improving or treating blemishes, and/or
- soothing skin, and/or
- decreasing or prevent skin redness, or skin inflammation, and/or
- decreasing skin sebum secretion, and/or
- decreasing visible lesions such as comedones, pustules and papules, and/or
- improving skin desquamation, in acneic skin, acne-prone skin or blemish-prone skin.

In some embodiments, the polylysine dendrimer is an unconjugated poly-L-lysine dendrigraft of second generation having a DPn from 40 to 60, preferably from 46 to 50, such as 48.

In some other embodiments, the polylysine dendrimer is a poly-L-lysine dendrigraft having a linear poly-L-lysine core wherein the ε-amino groups are substituted with a poly-L-lysine moiety. For instance, the linear poly-L-lysine core contains from 6 to 10, preferably 8 lysine residues in length and/or the poly-L-lysine moiety grafted on ε-amino groups have from 2 to 6, preferably 5 lysine residues in length.

In some further embodiments, the polylysine dendrimer is in the form of a polycationic dendrimer wherein the counter anion is acetate. An example of such a dendrimer is provided in FIG. 7.

The polylysine dendrimer may be present as an active ingredient in a non-medicinal, cosmetic or dermocosmetic composition. Examples of cosmetic compositions of interest encompass soothing cream, exfoliating product, daily cream or gel product, clarifying toner or lotion, purifying cleanser, blemish corrector cream or stick, and concealer stick or cream.

In some embodiments, the polylysine dendrimer may be used in combination with an active ingredient selected from vitamin A, retinoids such as adapalene, tretinoin, or tazarotene, bactericides such as benzoyl peroxide and decanediol, azelaic acid, salicylic acid, anti-inflammatory agents such as dapsone or *Melaleuca alternifolia* (Tea Tree) oil, anti-redness agents, soothing agents and combinations thereof.

The invention also relates to a topical composition for use in managing acneic skin, prone-acne skin or blemish-prone skin which comprises a polylysine dendrimer as an active ingredient and one or several excipients. The topical composition may comprise:
  from 0.1 to 100 ppm of a polylysine dendrimer, preferably as defined in any one of claims 7-10
  from 0% to 20% of one or more additional active agents, and
  from 70% to 99.9999% of one or more excipients, the percentages being expressed by weight relative to the total weight of the composition.

A further object of the invention is a method for treating or preventing acne in a subject, comprising a step of topically administering an effective amount of a polylysine dendrimer, or a composition thereof, to said subject. The invention also relates to a method for restoring or rebalancing microbiota in acne skin, in blemish-prone skin or in acne-prone skin, comprising a step of topically administering an effective amount of a polylysine dendrimer, or a composition thereof, to said subject.

The invention further relates to a method for improving skin aspect and feel, and/or restoring skin comfort and/or preventing, improving or treating blemishes and/or acne lesions and/or soothing skin, and/or diminishing the visibility of the pores (and thus smoothing the skin), and/or decreasing or preventing skin redness, and/or skin inflammation, and/or decreasing skin sebum secretion and/or making the skin with a less shiny and/or oily aspect, and/or improving skin in a subject with acne, with blemish-prone skin, or with acne-prone skin comprising a step of topically administering an effective amount of a polylysine dendrimer, or a composition thereof, to said subject.

The invention also relates to the use of a polylysine dendrimer, preferably a poly-L-lysine dendrimer in the manufacture of a topical composition for the management or the treatment of acne-prone skin, blemish-prone skin or acneic skin, as described above.

BRIEF DESCRIPTION OF THE DRAWINGS

FIGS. 5E and 5F show the *C. acnes* strain diversity using Simpson and Shannon index respectively after 28 days of treatment. The protocol and the results of the clinical trial are detailed in Example 8.

DETAILED DESCRIPTION OF THE INVENTION

Figure 1:
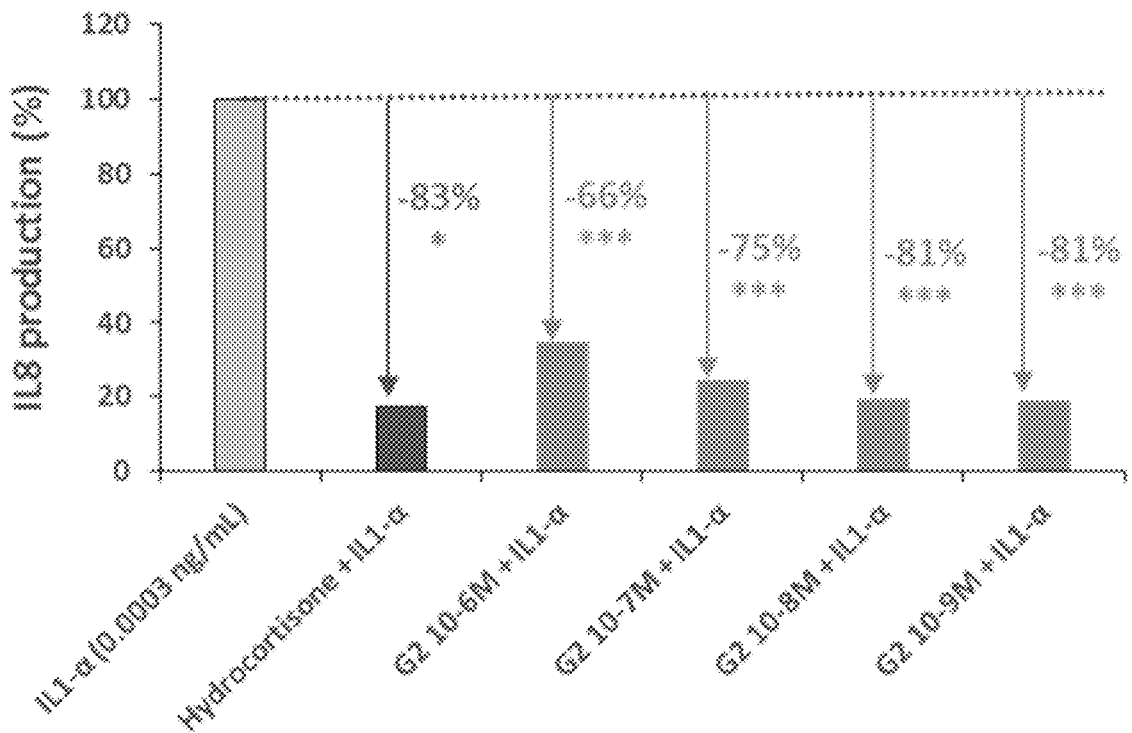
FIG. 1 shows the anti-inflammatory effect of a G2 dendrimer according to the invention in normal human dermis fibroblasts. Cells were treated with 0.0003 ng/mL IL-α in the presence of hydrocortisone (0.05 µg/mL) or G2 dendrimer ($10^{-9}$M, $10^{-8}$M, $10^{-7}$M or $10^{-6}$ M) and IL-8 production was determined by an IL-8 ELISA assay. *$p<0.05$, $p<0.01$, *$p<0.001$.

The Applicant showed that a "tree like" polymer of lysine residues, referred to herein as a "G2 dendrimer," exhibits antibacterial activity against an acneic *C. acnes* strain belonging to phylotype IA1 with a MIC of 20 ppm. In addition, the G2 dendrimer moderates the keratolytic effect and decreases the immune and inflammatory cascade known to be associated with *P. acnes* colonization. The Applicant further showed that this poly-L-lysine dendrimer was enabled to specifically target acneic strains of *C. acnes*. Of note, Example 6 showed that the G2 dendrimer significantly increases the membrane fluidity in acneic ribotypes belonging to phylotype IA1 (RT4 and RT5), while having no significant effect on non-acneic ribotype RT6 belonging to phylotype II. In other words, this result suggests that the G2 dendrimer is able to specifically destabilize cellular membrane of acneic strains, and thus inhibit their proliferation without impairing non acneic, *C. acnes* strains. Besides, Example 7 shows that the G2 dendrimer significantly decreases the biomass density in biofilm formed by acneic strain RT5 while having no significant effect on the biomass density in the biofilm formed by the non-acneic RT6 strain. The polylysine dendrimer is thus expected to reduce the inflammatory response triggered by *C. acnes* biofilm whatever the strain, by reducing the thickness of biofilm while exerting a selective and specific inhibitory action on acneic strains by destabilizing their biofilm.

The efficacy of G2 dendrimer of the invention to manage blemishes and lesions and improve skin microbiota in acneic skin was clinically confirmed. The Applicant showed that a treatment of 28 days with a cream containing a G2 dendrimer at a low concentration (2 ppm) significantly improved the aspect of the skin, in particular by decreasing the number of acne blemishes and lesions such as papules, pustules, blackheads and retentional lesions as compared to treatment with placebo cream. The G2-containing cream further enabled to decrease the sebum secretion rate of the skin. Of note, genomic analysis performed on face samples showed that G2 dendrimer-containing composition improved skin microbiota by increasing *C. acnes* strain diversity: the abundance of phylotype IA1 strains, identified as strains promoting acne in the literature, was decreased while that of non acneic phylotype II strains increased in samples from skin treated with the G2-containing composition. In other words, the polylysine dendrimer was shown to be an agent able to rebalance C. acneic diversity in acneic skins.

All together these results demonstrate that polylysine dendrimers are effective active agents to manage blemishes and restore skin microbiota in acne and acne-prone skin as well as in blemish-prone skin.

Accordingly, the present invention relates to the use of a polylysine dendrimer, preferably a poly-L-lysine dendrimer, as an active agent in the management of acneic skins, acne-prone skins and blemish-prone skins.

The invention also relates to the use of a polylysine dendrimer as an active agent in the prevention or in the treatment of vulgaris acne and/or in the management of blemishes and skin lesions associated with vulgaris acne.

The invention also relates to the use of a polylysine dendrimer, preferably a poly-L-lysine dendrimer, as an active agent:
- to improve skin aspect and feel, and/or
- to restore skin comfort and/or
- to prevent, improve or treat blemishes, and/or
- to prevent, improve or treat acne lesions and/or
- to soothe skin, and/or
- to diminish the visibility of the pores, and/or
- to decrease or prevent skin redness, or skin inflammation, and/or
- to decrease skin sebum secretion and/or make the skin with a less shiny and/or oily aspect
- decreasing visible lesions: blackhead, pustules and papules, and/or
- to improve skin desquamation (e.g. by exerting a keratolytic effect).

in a subject with a skin type selected from acne skin, acne-prone skin and blemish-acne skin.

The invention also relates to the use of a polylysine dendrimer, preferably to a poly-L-lysine dendrimer, to restore or rebalance microbiota in acne skin, in acne-prone skin or in blemish-prone skin. More precisely, the polylysine dendrimer of the invention is used as an agent for decreasing the abundance of acneic *C. acnes* strains in the skin, preferably in acne and prone-acne skins. In another or additional embodiment, the polylysine dendrimer of the invention is for increasing the abundance of non-acneic *C. acnes* in the skin, preferably in acne or prone-acne skins. The invention also relates to the use of a polylysine dendrimer to prevent or decrease skin colonization by acneic *C. acnes* strains. The invention further relates to the use of a polylysine dendrimer for increasing *C. acnes* diversity in acneic or acne-prone skin, e.g. by decreasing the abundance of *C. acnes* phylotype IA1 while enabling an increase in the abundance of *C. acnes* phylotype II or III.

In a more general aspect, the invention relates to the use of a polylysine dendrimer, preferably to a poly-L-lysine dendrimer, as an active agent for restoring skin microbiota balance, in particular in acne or acne-prone skins. In a further aspect, the invention relates to the use a polylysine dendrimer, preferably a poly-L-lysine dendrimer to prevent or treat skin dysbiosis associated with an unbalance in *C. acnes* population.

The invention also relates to the use of a polylysine dendrimer, preferably to a poly-L-lysine dendrimer, as an active agent for maintaining or restoring the skin microbiota homeostasis, especially in a subject having acneic skin, acneic-prone skin or blemish-prone skin.

A further aspect of the invention relates to a method for managing a skin type selected from acneic skin, acne-prone skin and blemish-prone skin in a subject which comprises a step of topically administering an effective amount of a polylysine dendrimer to said subject. Such a method enables to improve the aspect of the skin in the subject, e.g. by treating, decreasing and/or delaying the onset of skin blemishes and skin lesions in the subject.

The invention also relates to a method for treating or preventing acne in a subject, comprising a step of topically administering an effective amount of a polylysine dendrimer to said subject. Another object of the invention is a method for improving skin aspect and feel, and/or restoring skin comfort and/or preventing, improving or treating blemishes and/or acne lesions and/or soothing skin, and/or diminishing the visibility of the pores (and thus smoothing the skin), and/or decreasing or preventing skin redness, and/or skin inflammation, and/or decreasing skin sebum secretion and/or making the skin with a less shiny and/or oily aspect, and/or improving skin in a subject with acne skin, with acne-prone skin or with blemish-prone skin comprising a step of topically administering an effective amount of a polylysine dendrimer to said subject. The invention further relates to a method for restoring or rebalancing microbiota in acne skin or in acne-prone skin, comprising a step of topically administering an effective amount of a polylysine dendrimer to said subject.

The invention also relates to the use of a polylysine dendrimer, preferably a poly-L-lysine dendrimer, in the manufacture of a topical composition for the management or the treatment of acne-prone skin, blemish-prone skin or acneic skin, as described above.

The invention also provides topical compositions and methods for treating acne vulgaris, decreasing an inflammatory response in skin, and promoting desquamation of skin using a polylysine dendrimer, e.g. the G2 dendrimer, and/or a salt thereof. For instance, the invention relates to a method for decreasing an inflammatory response in skin comprising applying to the skin of a subject in need of treatment a composition comprising a polylysine dendrimer, e.g. an unconjugated poly-L-lysine dendrigraft, or a salt thereof, thereby decreasing an inflammatory response in the subject's skin, wherein the inflammatory response comprises IL-8 release or TLR2 overexpression in response to

*Cutibacterium acnes*. The invention further relates to a method for promoting desquamation of skin cells comprising applying to the skin of a subject in need of treatment a composition comprising a polylysine dendrimer, e.g. an unconjugated poly-L-lysine dendrigraft, or a salt thereof, thereby promoting desquamation of subject's skin cells.

The polylysine dendrimer according to the invention can be incorporated as an active ingredient in a topical composition, typically a pharmaceutical composition, a cosmetic composition or a dermocosmetic composition.

Typically, the polylysine dendrimer is present at a concentration from 0.1 ppm to 100 ppm, preferably from 0.1 ppm to 20 ppm, more preferably from 0.5 to 10 ppm, such as 0.5 to 7 ppm, e.g. from 0.5 to 6 ppm in a topical composition. The concentration of the polylysine dendrimer in the topical composition as well as the frequency of application of said topical composition can depend on the skin to treat and/or the stage of the treatment. For instance, a concentration of less than 4 ppm e.g. of 2 ppm may be sufficient for treating acne-prone skin, blemish-prone skin and skin with light acne, with an application once a day. For treating skin with moderate or severe acne, a higher concentration of the polylysine dendrimer can be used (e.g. from 4 to 10 ppm, e.g. 4 or 6 ppm) with application twice a day during the initial treatment. The dose and the frequency of application can be decreased once the skin lesions associated with acne are managed, and a maintenance treatment over several weeks can be implemented.

The polylysine dendrimer is typically used by topical route, e.g. applied to an area of the skin to be treated, e.g. a skin area afflicted with acne or a skin area with prone-acne profile or blemish-prone profile. Typically, the area of the skin to be treated may exhibit one or several skin blemishes and/or skin lesions as described below and/or an oily aspect (e.g. due to an excessive production of sebum). Skin area of interest encompasses, without being limited to, the face, the neck, the chest, the shoulders and the back.

The frequency of treatment can vary and depends on the skin type of the subject and/or the severity of acne if present. Generally, the polylysine dendrimer is applied to the skin to treat once or twice a day. The treatment with the polylysine dendrimer can last several consecutive days, e.g. from 7 to 28 days, or several months (at least 2, 3, 4, 6, 8 or 10 months).

Prolonged treatment with the polylysine dendrimer of the invention, especially at concentrations below 10 ppm, is expected to be well tolerated in the patient with any significant side effects such as skin irritation, at least because the polylysine dendrimer promotes the rebalance of skin microbiota by specifically targeting acneic strains of *C. acnes*.

The effects exerted by the dendrimer may be therapeutic, prophylactic and/or cosmetic depending on the skin type and the way of application.

For instance, the use of the polylysine dendrimer of the invention may be a cosmetic, non-therapeutic use when applied on a blemish-acne skin.

The subject may be of any subject suffering from acne or having an acne-prone or blemish-prone skin.

In some embodiments, the subject is a teenager from 10 to 18 years old, preferably from 12 to 16 years old.

In some embodiments, the subject suffers from acne and has more than 23 years old.

In another aspect, the subject is either a woman or a male of more than 23 years old.

In some other embodiments, the subject has acne-prone skin.

In some further embodiments, the subject suffers from light acne, moderate acne or severe acne, preferably from moderate or severe acne.

In a further embodiment, the subject has a blemish-prone skin.

As used herein, "a blemish prone skin" refers to a skin type wherein the skin has a propensity to develop some comedones and pimples, e.g. blackheads and whiteheads, without any inflammatory lesions such as papule and pustule.

"Blemish-prone skin" can be characterized by an oily and shiny aspect due to the fact that sebaceous glands produce more sebum than other skin types. Such increase in sebum production generally occurs during puberty when the production of hormone substances, called androgens, increases and in turn stimulates sebaceous glands to produce more sebum than is necessary. Certain hormonal treatments can also trigger skin sebum overproduction. This seborrhea may itself interfere also with the normal skin shedding and leads to skin blemishes. In some embodiments, a subject having a blemish-prone skin does not have a personal history of acne, especially severe or moderate acne. As used herein, an "Acne prone skin" refers to a skin type wherein the skin has a propensity to develop some comedones and pimples and even some very few inflammatory lesions (typically papules). In some embodiments, a subject with an acne-prone skin refers to a subject who has a personal history of acne, namely who has already experimented at least one episode of acne or who has a family history of acne, namely who has at least one family member (mother, father or sister/brother) who has experimented moderate or severe acne.

"Acne-prone skin" or "blemish-prone skin" does not stricto sensus refer to skins suffering from a skin disease but can degenerate into acne, if not properly managed.

As used herein, "acneic skin", also called herein "acne skin" refers to a skin afflicted with acne (also called acne vulgaris). Acne is a non-contagious, inflammatory skin disorder involving the pilosebaceous unit and characterized by pimples caused by inflamed and infected sebaceous glands. The disease is most common in adolescents, but symptoms can persist into adulthood and some people, especially women, experience symptoms for the first time after the age of 25. Persistent or late-onset acne is known as acne tarda. Acne typically appears on the face, neck, shoulders, chest and back. Acne ranges in severity from light acne (known as Acne Comedonica) through moderate acne (Acne Papulopustulosa) to severe acne (Acne Conglobata). Light acne is characterized by the presence of multiple blackheads, whiteheads, and sometimes few papules. Moderate acne is characterized by the presence of comedones, papules and pustules. The skin can appear red and inflamed. At last, severe acne is an uncommon form of acne characterized by multiple inflamed blemishes including papules and pustules which may group together and form nodules and cysts. The pathogenesis of acne is multifactorial and involves four key factors with interrelated mechanisms: increased sebum production, hyperkeratinization, skin inflammation, and *Cutibacterium acnes* proliferation.

As used herein, "blemishes" refer to any skin imperfection such as redness, pimples or comedones, e.g. to skin imperfections which can be observed in blemish-prone skin (or acne-prone skin), typically retentional lesions such as blackheads, whiteheads, and other pimples.

As used herein, "acne lesions" refer to inflamed, inflammatory lesions associated with acne e.g. papules, pustules, cysts and nodules observed in moderate and severe acne.

As used herein, acneic strains refer to *C. acnes* strains which are statistically more abundant in acneic skins than in healthy skins. *Cutibacterium acnes* has been sub-divided in six principal phylotypes namely IA1, IA2, 1B, IC, II and III (Dagnelie et al., 2018, supra). In skin, bacteria belonging to phylotype IA1 such as RT4 and RT5 ribotypes are predominant in acne skin. Acneic strains encompass phylotype IA1, 1A2, 1B and IC, preferably IA1 and IA2, more preferably IA1 such as ribotype I (RT1), ribotype 4 (RT4) and ribotype 5 (RT5).

Non-acneic strains refer to *C. acnes* strains which are statistically more abundant in healthy skin than in acneic skin. Such strains encompass phylotypes II and III such as ribotype RT6.

For more details concerning *C. acnes* phylotypes, clonal complex and single-locus sequence, one can refer to Dagnelie et al. (supra) and Scholz et al., 2016.

In some embodiments, treatment with the polylysine dendrimer of the invention decreases the abundance of *C. acnes* phylotype I strain in the total population of *C. acnes* present on the skin of the subject. In some other embodiments, treatment with the polylysine dendrimer of the invention increases the abundance of *C. acnes* phylotype II or III strains, preferably phylotype II, in the total population of *C. acnes* present on the skin of the subject.

As used herein, the terms "skin microbiota", "skin microbiome" or "skin flora" refer to the microorganisms which reside on the skin, typically human skin and encompass bacterial, mycobacterial, fungal and parasitic germs. Most are found in the superficial layers of the epidermis and the upper parts of hair follicles. Skin flora is usually non-pathogenic, and either commensal or mutualistic. The benefits that such microorganisms can offer include preventing transient pathogenic organisms from colonizing the skin surface, either by competing for nutrients, secreting chemicals against them, or stimulating the skin's immune system.

By "restoring or rebalancing" skin microbiota, it is meant restoring microorganisms diversity so as to get a balance in microorganism distribution promoting skin health and/or corresponding to healthy skin. In the context of the invention, "restoring or rebalancing microbiome" in blemish-prone skin, acne-prone skin or acneic skin or "restoring or rebalancing *C. acnes* distribution" means to decrease the abundance of acneic *C. acnes* strains on the skin. In some embodiments, it also encompasses promoting non acneic strains on the skin, e.g. by increasing their abundance. In some further embodiments, "restoring or rebalancing *C. acnes* distribution" means that the polylysine dendrimer of the invention enables to promote a *C. acnes* diversity while regulating *C. acnes* biomass density on the treated skin area, so as to obtain a *C. acnes* population close to, or similar to, that of the microbiome of a healthy skin, e.g. to that of a healthy skin area in the subject. It may also encompass the fact that the applied composition or active ingredient do not exert a significant lethal action on non-pathogenic, commensal, bacterial strains, in particular those of *C. acnes*.

The expression "decreasing the abundance of an acneic strain" means decreasing the amount/proportion of bacteria belonging to an acneic *C. acnes* strain as compared to the total amount of *C. acnes* bacteria present on a determined area of the skin of a subject, e.g. of a face area of a subject. The expression "increasing the abundance of a non acneic strain" means increasing the amount/proportion of bacteria belonging to a non acneic *C. acnes* strain as compared to the total amount of *C. acnes* bacteria present on a determined area of the skin of a subject, e.g. of a face area of a subject. A significant increase/decrease in the abundance/proportion of strain refers to a variation of at least 0.1%, such as of at least 1%, 2%, 3%, 5%, 10%, 15%, 20%, 25%, 30%, 35% or 45% of its abundance determined before treatment.

The abundance of *C. acnes* strains can be determined as shown in Example 8 by metagenomics performed on swabs from a skin aera of interest.

As used herein, by "increase the diversity of the microbiome", it is meant increasing the number of different bacterial strains present on the skin. More precisely, "increasing the diversity on *C. acnes*" means increasing the number and/or the abundance of non acneic strains on the skin.

As used herein, by "managing acne prone skin or blemish prone skin" it is meant improving the visual aspect of the acne-prone skin or blemish-prone skin, e.g. the skin has a less oily aspect, and/or exhibits less or reduced blemishes and pimples, and/or blemishes are less visible and/or the skin has a less propensity to exhibit blemishes with the treatment of the invention.

The expression "preventing" is intended to mean delaying or preventing the onset of the disorder of interest such as blemishes, acne lesions or acne.

The expression "treating a condition" is intended to mean decreasing, reducing, softening, correcting or slowing down the development of a condition of interest or associated manifestations thereof, e.g. acne and associated blemishes or lesions.

As used herein, "Dendrimers" are macromolecular highly branched compounds formed by reiterative reaction sequences starting from an initial core molecule with successive layers or stages being added in successive "generations" to build up a three-dimensional, highly ordered polymeric compound. The preparation of dendrimers has been described in the art, see, e.g., U.S. Pat. Nos. 4,289,872 and 4,410,688, which describe dendrimers based on layers of lysine units).

The dendrimer of the invention is a polylysine dendrimer, more preferably a poly-L-lysine dendrimer, such as a poly-L-lysine dendrigraft.

Like conventional dendrimers, the preparation of grafted dendrimers (also called herein dendrigraft) in a generation-based scheme involves protective group manipulation combined with polymerization steps, that is, either by cycles of protection, monomer polymerization, and deprotection (so-called "grafting from" method; Klok & Rodriguez Hernandez (2002) *Macromolecules* 35:8718-23) or by using pre-formed polymers instead of molecular compounds as $AB_n$ building blocks in cycles of protection, condensation and deprotection (so-called "grafting onto" method; Teertstra & Gauthier (2004) *Prog. Polym. Sci.* 29:277-327). Because G2 dendrimers are no longer single-molecule compounds, dendrigraft polymers have a less controlled structure than conventional dendrimers (e.g., as described in U.S. Pat. No. 4,289,872), but usually a more regular architecture compared to hyperbranched polymers (e.g., as described in Rodriguez-Hernandez, et al. (2003) *Biomacromolecules* 4:249-258 and Klok, et al. (2002) *Macromolecules* 35:8718-8723). Nevertheless, owing to their synthetic procedure, the molecular weight of grafted dendrimers increases more rapidly with each generation than that of dendrimers.

In some embodiments, the polylysine dendrimer according to the invention is a second generation (G2) grafted polylysine dendrimer, also referred to interchangeably herein as "G2 poly-L-lysine dendrigraft," "G2 dendrimer," "grafted dendrimer," "grafted polylysine dendrimer," or "grafted homopolylysine dendrimer," "lysine dendrigraft" or "DGL". It was shown that G2 dendrimer was more effective than linear polylysine to inhibit *C. acnes* proliferation and promote anti-inflammatory effect.

A G2 dendrimer of use in the methods of this invention can be prepared as described herein (Example 1) or as described, e.g., in US 2008/0206183 or Collet, et al. (2010) *Chem. Eur. J.* 16:2309-16.

In certain embodiments, the polylysine dendrimer, e.g. the G2 dendrimer, is a homopolylysine dendrigraft composed of 30 to 70 lysine residues, or more preferably 40 to 60 lysine residues, or most preferably 48 lysine residues. In certain embodiments, the polylysine dendrimer is a G2 dendrimer, said G2 dendrimer being a homopolylysine dendrigraft comprising, consisting of, or consisting essentially of 48 lysine residues. Preferably, as used herein, the number of lysine residues refer to the average degree of polymerization (DPn) of said dendrimer or dendrigraft.

In certain embodiments of this invention, the dendrimer of the invention is unconjugated. An "unconjugated" polylysine dendrigraft or dendrimer refers to a polylysine dendrigraft or dendrimer that has not been covalently attached or associated with another material such as a pharmaceutical or agricultural material, typically such as therapeutic moieties. In other words, the dendrimer of the invention may be devoid of any therapeutic, pharmaceutical or cosmetic moiety other than lysine. In some embodiments, lysine residue is the sole building block present in the polylysine dendrimer of the invention.

In some embodiments, the polylysine dendrimer of the invention is a dendrigraft comprising a linear polylysine core wherein the side chain $NH_2$ groups (ε-amino groups) of one or several (preferably all) lysine residues of said core are substituted with a polylysine moiety. For instance, the polylysine dendrigraft of the invention can comprise a linear poly-L-lysine core (i.e. a-poly-L-lysine) wherein the ε-$NH_2$ group of each lysine residue is substituted with a poly-L-lysine moiety, preferably a a-poly-L-lysine. The linear core may comprise from 2 to 10, e.g. from 6 to 10 lysine residues, e.g. 8 lysine residues in length and the poly-L-lysine substituents may comprise from 2 to 10 e.g. from 3 to 8 such as 5 lysine residues in length.

For instance, the polylysine dendrigraft of the invention may comprise compounds of formula (I):

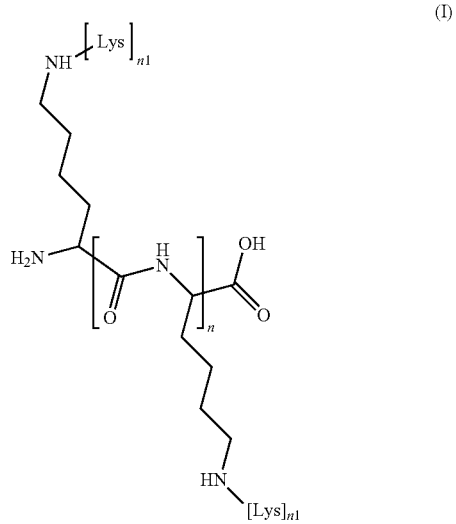

(I)

Wherein n is an integer from 2 to 10, e.g. 2, 3, 4, 5, 6, 7, 8, or 9, preferably 6, 7, 8 or 9, more preferably 7.

[Lys] denotes a lysine residue and n1 denotes the number of lysine moieties which is linked together to form a polylysine moiety, preferably α-polylysine moiety. each n1 are integers independently selected from 2 to 10, e.g. 2, 3, 4, 5, 6, 7 or 8, preferably 3, 4, 5, 6, or 7 and even more preferably from 4, 5 or 6. In some embodiments, all n1 are identical and are e.g. 5.

The average degree of polymerization (DPn) of the dendrigraft of the inventions is from 42 to 58, preferably from 46 to 50, more preferably about 48. As used herein, the average degree of polymerization (DPn) denotes the average number of lysine monomers per dendrimer molecule in the polylysine dendrimer according to the invention.

In some or further embodiment, the mass average molar mass (Mw) of the dendrigraft according to the invention is from 7500 to 10000, preferably from 8400 to 8800, such as 8600 g·mol$^{-1}$.

The polylysine dendrimer, including the G2 dendrimers of this invention, are polycationic polymers. While the G2 dendrimers synthesized and exemplified herein include trifluoroacetate (TFA) as a counter-anion, this anionic component can be exchanged with various other counter-anions such as bicarbonate, dihydrogen phosphate, fluoride, chloride, bromide, iodide, citrate, or acetate.

Accordingly, the present invention includes polylysine dendrimers such as G2 dendrimers, as well as salts thereof. Appropriate counter-anions are acetate, trifluoroacetate, chloride, citrate, phosphate, carbonate and combinations thereof, preferably acetate, chloride, carbonated and combinations thereof, more preferably acetate.

In certain embodiments, the counter-anion of the dendrimer is an acetate. Indeed, the Applicant showed that G2 dendrimer with acetate counter-anions has improved anti-inflammatory activity than G2 dendrimers with chloride or carbonate counter-anions in vitro: indeed, G2 dendrimer with acetate as counter-anions is more effective to manage 11-8 production following IL1-α stimulation in dermal fibroblasts in vitro.

To exchange the TFA counter-anions in acetate counter-anions, various methodologies are available. One method includes the use of a steric exclusion support (G25) in chromatographic mode with an ammonium bicarbonate elution buffer (0.1 M). After chromatography, the polymer is recovered in bicarbonate buffer and dried in a rotary evaporator thereby providing the polymer with a bicarbonate counter-anion. This counter-anion can then be exchanged with an acetate anion by neutralizing at pH 6.5 with acetic acid. The product is then dried by lyophilization. As an alternative, the polymer solution is dialyzed in an ammonium acetate buffer to exchange the TFA counter-anion. As a further alternative, the polymer is applied to an anion exchange resin previously conditioned in acetate. The performance of the exchange can be verified by $^{19}F$ NMR, by centesimal analysis or by search for TFA ions in LC/MS.

When used in the methods and uses of this invention, the polylysine dendrimer, e.g. the G2 dendrimer, and/or salt thereof, can be provided as a cosmetic active ingredient present in a cosmetic, pharmaceutical or dermocosmetic composition.

For instance a cosmetic composition encompasses, without being limited to, an anti-acne product, urban care product, smoothing cream, exfoliating product, daily protective product, a clarifying toner or lotion, a purifying cleanser, blemish corrector cream or stick, concealer stick, and the like. In some embodiments, the polylysine dendrimer is incorporated in a non-medicinal, cosmetic or dermocosmetic composition, for instance suitable for acne-prone skin or blemish-prone skin.

Accordingly, in certain embodiments, the polylysine dendrimer, e.g. the G2 dendrimer is a component of composition or formulation applied topically or locally to the skin. In certain embodiments, the composition is in the form of a cleanser, toner, lotion, solution, gel, cream, ointment, or foam. In this respect, a formulation or composition containing the polylysine dendrimer, e.g. the G2 dendrimer is suitable or adapted for topical or local application.

A composition containing a polylysine dendrimer according to the invention, e.g. the G2 dendrimer may be a viscous or semi-viscous fluid, or a less viscous fluid such as might be used in sprays or aerosols. It may take the form of a solution, suspension or emulsion. It may take the form of a solid such as a powder or granules, which may be designed to be added to liquid (e.g., water) prior to use. In some embodiments the formulation is, or may be, applied to a carrier such as a sponge, swab, brush, pad, tissue, cloth, wipe, skin patch or dressing (which includes a bandage, plaster, skin adhesive or other material designed for application to a tissue surface), to facilitate its administration.

A composition according to the invention may be intended for pharmaceutical (which includes veterinary but is preferably human) use, and/or for cosmetic, dermocosmetic or other non-medical care purposes (for example, to cleanse the skin, or to improve the appearance, feel or smell of the skin).

A composition according to the invention may contain excipients and other additives known for use in topical formulations. Suitable excipients for use in formulations designed for topical or local application will be well known to those skilled in the art. Those included will depend on the intended mode and site of application for the formulation. In the context of formulations for topical application to the skin, examples may for instance be found in Williams' *Transdermal and Topical Drug Delivery* (Pharmaceutical Press, 2003) and other similar reference books. See also Date, et al. ((2006) *Skin Pharmacol. Physiol.* 19(1):2-16) for a review of topical delivery strategies, and also *Skin Delivery Systems* ((2006) John J Wille, Ed, Blackwell Publishing.

The excipient(s) used may be suitable for targeting or controlling release of the composition, or of a component of the composition, at the intended site of administration, for instance to target a desired site and/or time of delivery. Such excipients may for instance target the composition to a region of the skin, for example the stratum corneum or the pilosebaceous follicles, or to hair follicles. They may delay or otherwise control release of the composition over a particular time period.

Where the composition is intended for topical application to the skin, examples of suitable additives, also referred as excipients, include diluents, fillers, carriers, emollients, moisturizers, perfumes, antioxidants, preservatives, stabilizers, gelling agents and surfactants; and/or other substances commonly used in formulation in the cosmetics or pharmaceutical field. Others may be found in Williams' *Transdermal and Topical Drug Delivery* (see above). For the treatment of acne, however, it may be preferred for the composition not to contain an emollient.

The polylysine dendrimer, e.g. the G2 dendrimer, and/or salt thereof, may be used individually or together, or may be used in combination with one or more additional active ingredients such as antimicrobial (in particular antibacterial) agents or anti-inflammatory agents. The additional active ingredients can be combined with the polylysine dendrimer in one single composition, or administered separately, including by a different route (e.g. by oral route).

In some embodiments, said additional active ingredient(s) and the polylysine dendrimer are combined within the same composition.

For example, said formulation may contain one or more agents selected from anti-acne agents, keratolytics such as lactic acid, comedolytics, agents capable of normalizing keratinocyte and/or sebocyte function, anti-inflammatories such as Licochalcone A and *Glycyrrhiza Inflata* extract, anti-proliferatives, antibiotics, anti-androgens, sebostatic/sebosuppressive agents (also known as seboregulator) (e.g., a natural extract of *Backhousia citriodora*), anti-pruritics, immunomodulators, anti-irritant or soothing (e.g., an extract of *Epilobium angustifolium*), agents which promote wound healing, sunscreens, skin lightening agents, anti-aging substances, and mixtures thereof.

For instance, anti-acne agents encompass, without being limited to, vitamin A, retinoids such as adapalene, tretinoin, or tazarotene, bactericides such as benzoyl peroxide and decanediol, antibiotics such as clindamycin or erythromycin, azelaic acid, salicylic acid, anti-inflammatory agents such as dapsone or *Melaleuca alternifolia* (Tea Tree) Oil and combinations thereof.

By way of example of sebum regulators, one can cite flax lignans, rice powder, zinc gluconate, sarcosine, an extract of *Cinnamomum zeylanicum* bark, an extract of avocado, Extract from the Australian *Backhousia citriodora* leaf, *Trifolium pratense* (Clover) Flower Extract and combinations thereof.

By way of anti-redness agents, one can cite saponins, flavonoids, ruscogenins, esculosides, and extracts containing them, for example extracts of Ruscus, and also certain essential oils, for example of lavender or of rosemary.

By way of example of soothing agents, one can cite allantoin, extracts of aloes, of *Calendula officinalis*, of birch (for example *Betula alba*), of willowherb (*Epilobium angustifolium*), of Tasmania Pepper (for example Tasmania *Lanceolata*), of chestnut (for example *Castenea sativa*), of cornflower (for example *Centaurea cyanus*), of *Centella* (for example *Centella asiatica*), of field horsetail (for example *Equisetum arvense*), of fennel (for example *Foeniculum vulgare*), of common witch hazel (for example *Hamamelis virginiana*), of ivy (for example *Hedera helix*), of *Habiscus sabdariffa*, of lily (for example *Lilium candidum*), of common mallow (for example *Malva sylvestris*), of lemon balm (for example *Melissa officinalis*), of skullcap (for example *Scutellaria baicalensis*), of *Mimosa* (for example *Mimosa tenuiflora*), of cinquefoil (for example *Potentilla erecta*), an extract of exopolysaccharide from an extremophil (for example *Alteromonas* ferment) an extract of oligosaccharides or an oligosaccharide, for example of flax, peptides such as palmitoyl tripeptide-8, and combinations thereof.

For instance, the polylysine dendrimer may be present in a composition. Said cosmetic composition may comprise one or more excipients and optionally one or more additional active agents having a cosmetic or a pharmaceutical effect.

In some embodiments, the additional active agent(s) present in the composition is/are a cosmetic active ingredient.

The expression "cosmetic active agent" refers to a compound capable of exerting at least one cosmetic effect on the skin. The term "cosmetic effect" is intended to mean any non-therapeutic effect aiming at modifying and/or improving the appearance or the feel of the skin, protecting them from outside attacks (sun, wind, moisture, dryness, chemical products), or preventing and/or correcting phenomena associated with ageing or puberty.

Typically, said composition comprises:
from 0.1 to 100 ppm of a polylysine dendrimer of the invention
from 0% to 20% of one or more additional active agents, and
from 70% to 99.9999% of one or more excipients,
the percentages being expressed by weight relative to the total weight of the composition.

Preferably said composition is a cosmetic or dermocosmetic composition.

In some embodiments, the polylysine dendrimer, e.g. the G2 dendrimer, is used in a synergistic combination with an antimicrobial and/or anti-inflammatory agent thereby permitting a reduction in the dosage of one or both agents in order to achieve a similar or improved effect. This would allow the use of smaller doses and, therefore, would decrease the potential incidence of toxicity and lowering costs of expensive antimicrobials.

In this context an additional antimicrobial agent may be selected from a biocide, disinfectant, antiseptic, antibiotic, bacteriophage, enzyme, anti-adhesin, immunoglobulin, antimicrobially active antioxidant, and mixtures thereof; it may be active as a bactericide, in particular against propionibacteria. In certain embodiments, the antimicrobial agent is an antibiotic such as a penicillin, cephalosporin, carbacephem cephamycins, carbapenem, monobactam, aminoglycoside, glycopeptide, quinolone, tetracycline, macrolide, or fluoroquinolone. Examples of particular antibiotic agents include, but are not limited to, Penicillin G, Methicillin, Nafcillin, Oxacillin, Cloxacillin, Dicloxacillin, Ampicillin, Amoxicillin, Ticarcillin, Carbenicillin, Mezlocillin, Azlocillin, Piperacillin, Imipenem, Aztreonam, Cephalothin, Cefazolin, Cefaclor, Cefamandole formate sodium, Cefoxitin, Cefuroxime, Cefonicid, Cefmetazole, Cefotetan, Cefprozil, Loracarbef, Cefetamet, Cefoperazone, Cefotaxime, Ceftizoxime, Ceftriaxone, Ceftazidime, Cefepime, Cefixime, Cefpodoxime, Cefsulodin, Fleroxacin, Nalidixic acid, Norfloxacin-Ciprofloxacin, Ofloxacin, Enoxacin, Lomefloxacin, Cinoxacin, Doxycycline, Minocycline, Tetracycline, Amikacin, Gentamicin, Kanamycin, Netilmicin, Tobramycin, Streptomycin, Azithromycin, Clarithromycin, Erythromycin, Erythromycin estolate, Erythromycin ethyl succinate, Erythromycin glucoheptonate, Erythromycin lactobionate, Erythromycin stearate, Vancomycin, Teicoplanin, Chloramphenicol, Clindamycin, Trimethoprim, Sulfamethoxazole, Nitrofurantoin, Rifampin, Mupirocin, Metronidazole, Cephalexin, Roxithromycin, Co-amoxiclavuanate, combinations of Piperacillin and Tazobactam, and their various salts, acids, bases, and other derivatives, and combinations thereof.

The polylysine dendrimer, e.g. the G2 dendrimer, and/or salt thereof, may also be used in combination with an antifungal agent. Exemplary antifungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

The polylysine dendrimer, e.g. the G2 dendrimer, and/or salt thereof, may also be used in combination with an antiviral agent. Exemplary antiviral agents include, but are not limited to, amantadine hydrochloride, rimantadin, acyclovir, famciclovir, foscarnet, ganciclovir sodium, idoxuridine, ribavirin, sorivudine, trifluoridine, valacyclovir, vidarabine, didanosine, stavudine, zalcitabine, zidovudine, interferon alpha, and edoxudine.

The polylysine dendrimer, e.g. the G2 dendrimer, and/or salt thereof, may also be used in combination with an antiparasitic agent. Exemplary antiparasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

As noted above, the polylysine dendrimer, e.g. the G2 dendrimer, and/or salt thereof, may be used in a synergistic combination with other known anti-inflammatory agents. Anti-inflammatory agents include, without limitation, corticosteroids (e.g., hydrocortisone, triamcinolone), non-steroidal anti-inflammatory drugs (NSAIDs) (e.g., nabumetone, indomethicin, naproxen, ibuprofen), anti-inflammatory cytokines (e.g., IL-4, IL-10, IL-13), cytokine antagonists (e.g., IL-1 receptor antagonist, TNF-α monoclonal antibody, soluble TNF receptor, platelet factor 4), and the like. See also, e.g., U.S. Pat. Nos. 6,190,691; 5,776,892; 4,816,449; and U.S. RE37,263.

A formulation of use in the methods of this invention may be incorporated into, and hence applied in the form of, a cosmetic; a skin care preparation (for example a skin cleanser, toner or moisturizer); a deodorant or anti-perspirant; a cleansing preparation (for example a facial wash); a pharmaceutical (which includes veterinary) preparation; a cosmeceutical preparation; a toiletry product (for instance a bath or shower additive or a soap). The formulation may be, or be incorporated into, a wash-off skin treatment product such as a skin cleanser, or in particular a leave-on skin treatment product.

As described herein, the polylysine dendrimer, e.g. the G2 dendrimer, and/or salt thereof, exhibits antibacterial activity and decreases adhesion of certain *C. acnes* strains to skin cells. Accordingly, one aspect of this invention is a method for treating acne vulgaris by applying to the skin of a subject in need of treatment an antibacterial-effective amount of a composition containing an unconjugated poly-L-lysine dendrigraft, and/or a salt thereof.

As used herein, "an antibacterial active" refers to an active able to prevent or decrease the growth and the proliferation of *C. acnes*, preferably acneic *C. acnes* strains.

As mentioned above, "acne" or "acne vulgaris" is a multifactorial disease of the pilosebaceous follicles of the face and upper trunk, characterized by a variety of inflamed and non-inflamed lesions such as papules, pustules, nodules and open and closed comedones. Its treatment can therefore encompass the treatment (which embraces prevention or reduction) of any of these symptoms, and references to use as an anti-acne agent may be construed accordingly. In particular, the treatment of acne encompasses the treatment (including prevention) of lesions associated with acne. It also encompasses the inhibition of propionibacterial activity which could cause or be otherwise associated with acne or its symptoms. In the context of the present invention, it may in particular be the treatment of inflamed acne lesions.

Treatment of acne encompasses both therapeutic and prophylactic treatment, in either a human or animal but in particular a human. It may involve complete or partial eradication of the condition, removal or amelioration of associated symptoms, arresting subsequent development of the condition, and/or prevention of, or reduction of risk of, subsequent occurrence of the condition. It will particularly involve the use of an unconjugated G2 dendrimer, and/or salt thereof, as described herein. In certain embodiments, the method encompasses treatment of acne vulgaris associated with *C. acnes* present on facial skin.

Another aspect of this invention is directed to a method for decreasing an inflammatory response in skin by applying to the skin of a subject in need of treatment a composition containing an unconjugated poly-L-lysine dendrigraft, and/or a salt thereof. In certain embodiments, the inflammatory response includes IL-8 release or TLR2 overexpression in response to *P. acnes*. Measurable decreases in IL-8 release or TLR2 overexpression can be assessed using any conventional technique or those exemplified herein. Preferably, the polylysine dendrimer, e.g. the unconjugated poly-L-lysine dendrigraft, and/or salt thereof, provides at least a 5%, 10%, 15%, 20%, 25%, 30%, 35%, 40%, 45%, 50%, 55%, 60%, 65%, 70%, 75% or 80% reduction in IL-8 protein production and/or TLR2 overexpression as compared to skin not contacted with the unconjugated poly-L-lysine dendrigraft, and/or salt thereof.

A further aspect of this invention is a method for promoting desquamation of skin cells by applying to the skin of a subject in need of treatment a composition containing a polylysine dendrimer, e.g. an unconjugated poly-L-lysine dendrigraft, and/or a salt thereof. Desquamation is a natural phenomenon associated with the fact that the epidermis, which constitutes the upper layer of the skin, is constantly regenerating. During the normal process of desquamation, the uppermost corneocytes detach from the surface of the epidermis. In accordance with the present method, application of a polylysine dendrimer, e.g. an unconjugated poly-L-lysine dendrigraft to the surface of the skin promotes desquamation and/or stimulates the epidermal renewal process.

"Applying," "application," "administering" or "administration" of a composition containing a polylysine dendrimer, e.g. an unconjugated G2 dendrimer and/or salt thereof to the skin of a subject embraces topical or local skin treatment with the composition. In certain embodiments, the polylysine dendrimer, e.g. the G2 dendrimer and/or salt thereof is applied to the facial skin of a subject.

A subject in need of treatment with a composition containing a polylysine dendrimer, e.g. a G2 dendrimer and/or salt thereof refers to any subject at risk of, predisposed to, or having a condition in which the G2 dendrimer and/or salt thereof would provide a benefit, e.g., anti-acne activity, anti-inflammatory activity or keratolytic activity. In some embodiments, the methods of the present invention are particularly useful in decreasing acne problems in teenagers, decreasing skin inflammation and improving the appearance or feel of adult skin.

An effective amount of a composition containing a polylysine dendrimer, e.g. an unconjugated G2 dendrimer and/or salt thereof may refer to an amount that provides a measurable inhibition of bacterial growth, whether completely or partially, of one or more acneic *C. acnes* strains; a measurable decrease in an inflammatory response, e.g., IL-8 release or TLR2 overexpression in response to *C. acnes*; and/or measurable desquamation of skin cells. It may also refer to an amount enabling to improve or treat blemishes in acneic or prone-acne skin.

An effective amount of a composition containing a polylysine dendrimer, e.g. an unconjugated G2 dendrimer, and/or salt thereof, includes between about 0.01 ppm to about 100 ppm, or more preferably about 0.1 ppm to 50 ppm, or most preferably about 1 ppm to 10 ppm of the polylysine dendrimer, e.g. the unconjugated G2 dendrimer, and/or salt thereof.

In certain aspects, the use of a composition of the invention is for non-therapeutic purposes. In accordance with this aspect, the composition is used as an anti-acne/anti-inflammatory or in particular a skin care agent for non-therapeutic purposes, for example for cosmetic purposes such as to improve the appearance or feel of the skin, in particular facial skin.

The invention is described in greater detail by the following non-limiting examples.

Example 1: Synthesis of DGL G2

The synthesis of the first generation of poly(L-lysine) was carried out by a three-step sequence (Scheme 1).

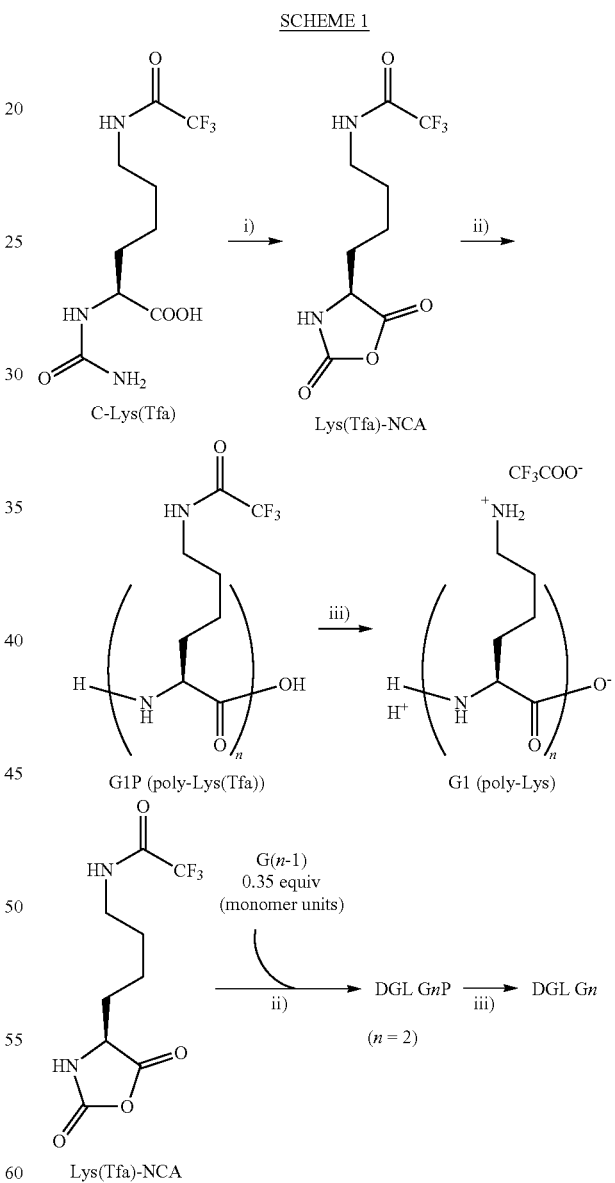

SCHEME 1 i) NO, $O_2$, MeCN, 0° C., 1 h;
ii) NaHCO$_3$ (0.2N), 0° C., 15 h;
iii) NH$_3$, H$_2$O/MeOH, 40° C., 15 h.

N-carbamoylation of Nε-trifluoroacetyl-L-lysine provided C-Lys(Tfa). NO-mediated nitrosation of C-Lys(Tfa) in acetonitrile gave monomer Lys(Tfa)-NCA, which was then reacted in aqueous sodium hydrogen carbonate (pH 6.5) to give Nε-protected oligo(L-lysine) G1P. Both nitrosation and polycondensation steps were carried out in one pot without isolating the NCA intermediate and the resulting polymer, G1P, spontaneously precipitated from the reaction medium. The G1P polymer was isolated by filtration and ε-amino groups were deprotected by alkaline treatment of G1P with ammonia in methanol/water. Deprotection yielded oligo(L-lysine) G1 with a DPn of approximately 8 in 50-60% overall yield from C-Lys(Tfa).

Dendritic materials were subsequently prepared by implementing the above-described reaction sequence in a multi-generation sequence (Scheme 1). Upon reacting crude Lys (Tfa)-NCA in aqueous NaHCO$_3$ in the presence of poly(L-lysine) G1 (30% w/w; 0.36 equiv in monomer units), polymer G2P spontaneously precipitated from the reaction medium, which, after isolation, underwent alkaline Nε-deprotection to afford poly(L-lysine) G2 with a DPn of about 48 and 36% overall yield from C-Lys(Tfa). Subsequently, ion exchange was carried out to convert trifluoroacetate salt into acetate salt.

Example 2: Inhibition of *C. acnes* by G2 Dendrimer

The effectiveness of G2 dendrimer for inhibiting the growth of *C. acnes* in culture was assessed. G2 dendrimer was used at a final concentration ranging between $10^{-2}$ M and $10^{-5}$ M. Experiments were performed using *C. acnes* strain IP 53117T (see FR2844715 A1), a strain known to cause acne. This strain belongs to a ribotype 1 (RT1) from phylotype 1A1 and is thus an acneic strain.

Bacteria ($10^8$ CFU/ml) were inoculated in 96-well plates containing a range of G2 dendrimer concentrations. After incubation for 24 to 48 hours at 37° C., the MIC (minimum inhibitory concentration) was defined visually as the lowest concentration with no visible growth. Based upon the results of two separate experiments, this analysis indicated that the MIC of the G2 dendrimer for *C. acnes* strain IP 53117T was $1.6$-$2.3 \times 10^{-5}$ M (10-20 ppm). Accordingly, G2 dendrimer significantly inhibits the growth against the tested acneic *C. acnes* strain and thus exhibits bactericidal effects at high dose (20 ppm).

Example 3: Effect of G2 Dendrimer on *C. acnes* Adhesion in Keratinocyte Culture The initial stage of acne vulgaris is establishment of the bacteria on the skin surface, i.e., colonization. Colonization is dependent upon bacterial adhesion. Accordingly, it was determined whether the G2 dendrimer could inhibit adhesion of acneic *C. acnes* strain to keratinocytes in culture.

Keratinocytes were isolated from the human epithelial cell line NCTC 2544 (Neufahrt, et al. (1978) *Arch. Dermaol. Res.* 256(3):255-60). Culture were maintained with Dulbecco's modified Eagle's medium (DMEM) containing 10% fetal calf serum, 1% antibiotics (penicillin/streptomycin), and 1% L-glutamine at 37° C. under 5% $CO_2$ and 95% humidity.

To monitor bacterial adhesion, adenine of the IP 53117T bacterial strain (belonging to acneic phylotype IA1) was labeled with tritium and bacterial adhesion to the surface of keratinocytes was determined by counting the radioactivity.

Method 1. Labeled bacteria ($2 \times 10^8$ microorganisms/mL) were combined with varying amounts of G2 dendrimer (final concentration between $10^{-5}$M and $6.25 \times 10^{-6}$ M) and deposited on the surface of a monolayer of keratinocytes. After incubation for 2 hours (37° C., 5% $CO_2$), cells were washed with phosphate-buffered saline (PBS) to remove non-adherent bacteria.

Method 2. The keratinocytes were pretreated for 24 hours with the G2 dendrimer. Labeled bacteria ($2 \times 10^8$ microorganisms/mL) was then added to the cell monolayer for 2 hours without prior removal of the G2 dendrimer.

The results of this analysis indicated that after 2 hours, the dendrimer inhibited the adhesion of *C. acnes* on keratinocyte surfaces by 50%, 40% and 29% at $10^{-5}$ M, $5 \times 10^{-6}$ M and $2.5 \times 10^{-7}$ M, respectively, compared to adhesion of *C. acnes* in the absence of G2 dendrimer. After a 24-hour pretreatment, the G2 dendrimer inhibited the adhesion of *C. acnes* on keratinocyte surfaces by 50%, 51% and 35% at $10^{-5}$M, $5 \times 10^{-6}$ M and $2.5 \times 10^{-6}$ M, respectively compared to adhesion of *C. acnes* in the absence of G2 dendrimer. Based upon the results of these two assays (concomitant or pretreatment), the G2 dendrimer was shown to exhibit strong anti-adhesion activity. Therefore, the G2 dendrimer is of use in blocking the initial stage of acne vulgaris, i.e., by preventing excessive bacterial adhesion or colonization by acneic strains.

Example 4: Effect of G2 Dendrimer on Inflammation in Normal Human Dermal Fibroblasts There is evidence that *C. acnes* is involved in invoking an inflammatory response. In particular, stimulation of Toll-like receptor 2 (TLR2) by *C. acnes* has been shown to result in increases in the Interleukin 8 and 12 (IL-8 and IL-12) concentrations (Kim, et al. (2002) *J. Immunol.* 169(3):1535-41). Therefore, the effect of the G2 dendrimer on inflammation in normal human dermis fibroblasts (NHDF) was assessed. NHDF were isolated from human dermis and maintained in DMEM containing 10% fetal calf serum, 1% antibiotics (penicillin/streptomycin) and 1% L-glutamine at 37° C. under 5% $CO_2$ and 95% humidity.

IL-8 mediates inflammatory reactions in the skin through the recruitment of neutrophils and other immune cells to invade injured or inflamed tissue. IL-8 secretion is inducible in cultured human dermal fibroblasts following activation with the pro-inflammatory cytokine IL-1a (Larsen, et al. (1989) *Immunology* 68(1):31-6). Accordingly, non-confluent NHDF cells were treated with IL1-α (0.1 ng/mL), as an inducer of IL-8 production, in the presence or absence of G2 dendrimer ($10^{-9}$M, $10^{-8}$M, $10^{-7}$M or $10^{-6}$ M) or hydrocortisone (0.05 μg/mL) as the positive anti-inflammatory control. IL-8 release from fibroblasts was determined by enzyme-linked immunosorbent assay (ELISA).

The results of this analysis (FIG. 1) indicate that hydrocortisone decreased IL-8 production by 83%. Under the same experimental conditions, G2 dendrimer reduced IL1-α-induced IL-8 production by 66 to 81%. Therefore, G2 dendrimer can attenuate the inflammatory cascade in human dermal fibroblasts known to be associated with *C. acnes* colonization.

Example 5: G2 Dendrimer Anti-Acne and Keratolytic Activity in Human Skin Explants To demonstrate the anti-acne and keratolytic activity of the G2 dendrimer, human skin explants were exposed to freeze-dried *P. acnes* (*C. acnes* strain IP 53117T-RT1-phylotype IA1) to ex vivo simulate in vivo acne.

Figure 2:
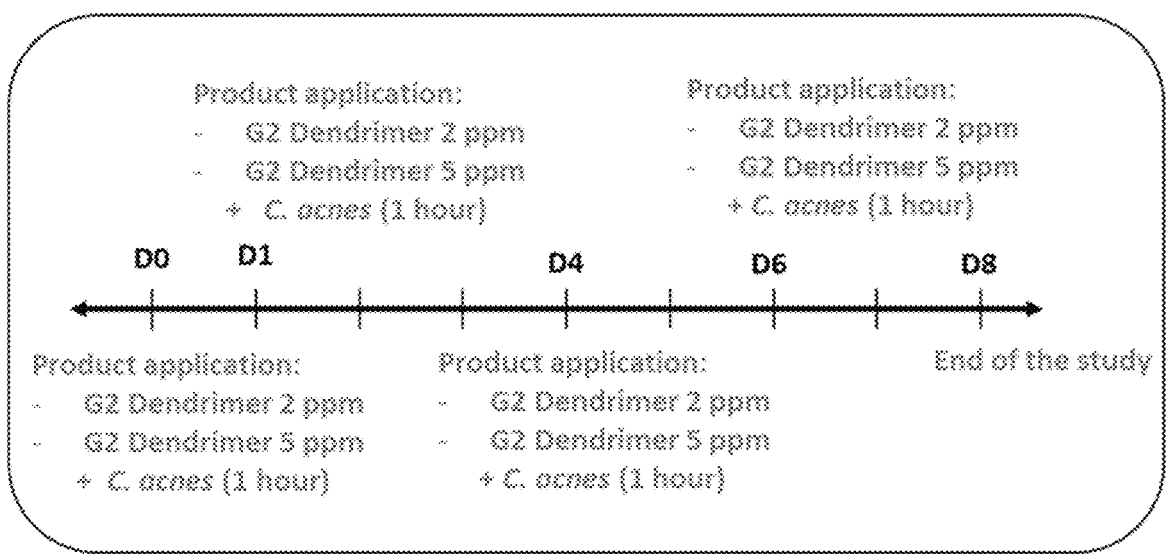
FIG. 2 is a schematic showing the timeline of product application in an ex vivo model of acne vulgaris used in Example 5. The G2 dendrimer was applied at 2 ppm or 5 ppm followed by *C. acnes* (1 hour) at D0, D1, D4 and D6.

Skin Treatment. Fifteen human skin specimens were obtained from patients undergoing plastic surgery (Caucasian women, 26 years old). Skin explants were maintained in culture for 8 days. A 1-hour treatment with G2 dendrimer (2 and 5 ppm) was concomitant with application of freeze-dried *C. acnes* (30 µL) at days 0, 1, 4 and 6 (FIG. 2). At day 8, explants were fixed and embedded in paraffin. Thick sections of 5 µm were stained with Masson's Trichrome stain or an anti-TLR2 antibody.

Evaluation of Keratolytic Effect. The general morphology and in particular stratum corneum of the explants were analyzed. Images were taken with a Leica Orthoplan microscope equipped with a digital camera (tri-CCD) driven by the acquisition and archiving software Leica IM1000.

Immunostaining of TLR2 TLR2 is known to mediate the inflammatory response of skin to acne (Kim, et al. (2002) 1 Immunol. 169(3):1535-41; McInturff & Kim (2005) *Semin. Cutan. Med. Surg.* 24(2):73-8). Accordingly, TLR2 protein in frozen sections was assessed with an anti-TLR2 (clone TL2.1; Santa Cruz). Sections were incubated with a 1:25 dilution of the anti-TLR2 antibody overnight at 4° C. and antibody binding was subsequently detected with biotin/streptavidin-FITC conjugate. Nuclei were stained with propidium iodide.

Quantification of IL1-α Cytokine. The concentration of IL1-α in the culture media was determined using an ELISA assay kit (Cayman, Ann Arbor, MI). The absorbances were measured using a microplate reader Tecan Infinite M200 Pro, combined with Magellan's software.

Results. Topical application of G2 dendrimer at 2 ppm induced a moderate separation of the upper layers of the stratum corneum with lower layers remaining more laminated. By comparison, application of 5 ppm G2 dendrimer induced a lower detachment. In light of this keratolytic activity, G2 dendrimer is of use in promoting skin desquamation.

With respect to TLR2 expression, topical application of G2 dendrimer at 2 and 5 ppm resulted in a complete inhibition of TLR2 overexpression induced by C. Acnes.

Figure 3:
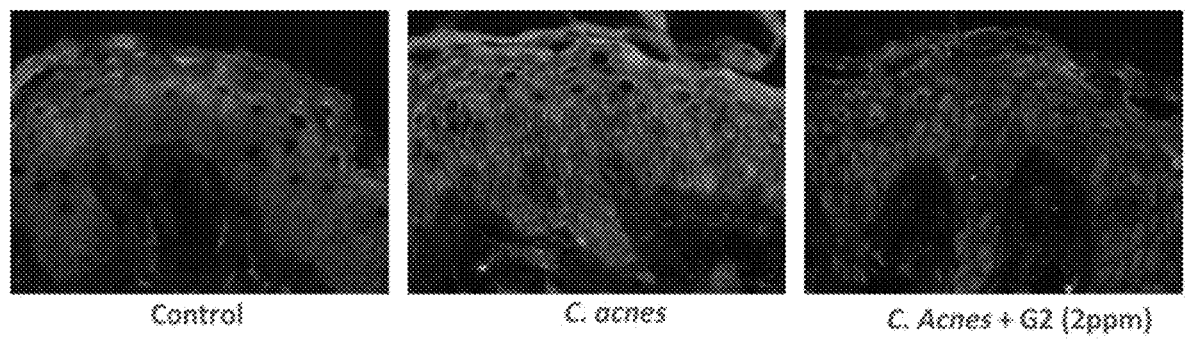
FIG. 3 shows the effect of the G2 dendrimer on TRL2 expression in human skin explants challenged with *C. acnes*. Explant without treatment with *C. acnes* or G2 was used as control.

To assess inflammatory responses, IL1-α production was quantified (FIG. 3). At day 1 (D1), *C. acnes* did not induce a significant increase in IL1-α production, compared to the control condition (i.e., the explant without treatment). Further, compared to treatment with *C. acnes*, the G2 dendrimer significantly decreased IL1-α production by 49% and 42% at 2 and 5 ppm, respectively, at day 1. After 4 days of survival (D4), the release of IL1-α decreased significantly by 53% in the control condition. Furthermore, compared to treatment with *C. acnes*, 2 ppm and 5 ppm G2 dendrimer provided a decrease in IL1-α production (28% and 27%, respectively) at day 4. Therefore, G2 dendrimer reduces *C. acnes* growth, dims the immune and inflammatory cascade for optimal skin protection, and provides a keratolytic effect.

Example 6: G2 Dendrimer Selectively Increases the Membrane Fluidity in *C. acnes* Strains Belonging to *C. acnes* Phylotype The impact of G2 dendrimer on the membrane fluidity of three bacterial strains of *Cutibacterium acnes* was tested. Two of the tested strains of *C. acnes* are "acneic" strains belonging to phylotype IA1 (RT4 and RT5) while the last one is a non-acneic strain (RT6) belonging to phylotype II. Several colonies of RT4, RT5 and RT6 (*C. acnes* strains) were scrapped and put in reinforced clostridial medium (RMC medium). The tubes were vortexed few seconds and homogenized before to be completely filled out with RMC in order to create anaerobic state. The tubes were then incubated at 37° C. for at least 48 h.

Bacterial cultures were collected and the OD was taken at 580 nm. After inoculation, the bacteria were sending in microplate and treated or not with G2 dendrimer. After 2 hours in anaerobic chamber, the plate was transferred in microplate reader for 72 h (OD 580 nm with measurement every 30 min). Then, the generation time of the bacteria was analyzed for each *C. acnes* strains. The G2 Dendrimer was tested at the following concentrations: $6 \cdot 10^{-6}$M, and $6 \cdot 10^{-7}$M.

—Results

Figure 4:
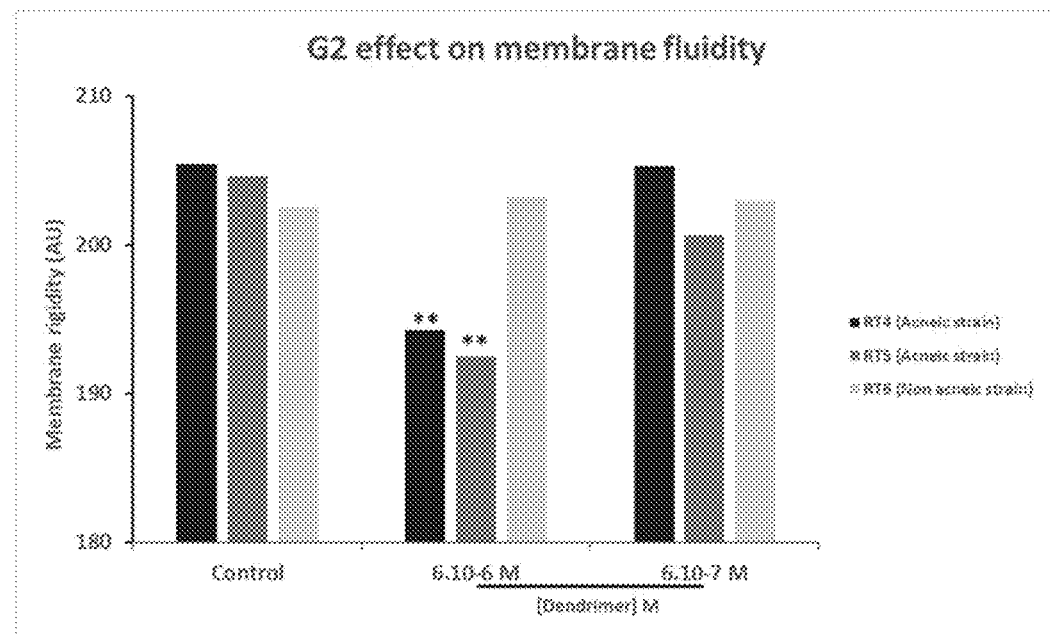
FIG. 4 shows the effect of the G2 dendrimer on the membrane fluidity of acneic strains of *C. acnes* (RT4 and RT5) and non-acneic strains of *C. acnes* (RT6). The G2 dendrimer specifically and significantly increases membrane fluidity in acneic strains.

The results are shown in FIG. 4. After 72 h of incubation, G2 dendrimer (at $6 \cdot 10^{-6}$M) significantly decreased the membrane rigidity of acneic strains RT4 and RT5 as compared to control. Of note, G2 dendrimer does not exhibit any significant effect on RT6 strain at $6 \cdot 10^{-6}$ M. In other words, G2 dendrimer exhibits a specific effect on membrane fluidity in acneic strains RT4 and RT5 as compared to non-acneic strain (RT6).

Such increase in membrane fluidity is expected to destabilize bacterial membrane of acne strains of acneic phylotype IA1 and thus, limits their growth while maintaining and even promoting non-acneic phylotype strains of phylotype II.

Example 7: Effects of G2 Dendrimer on Biofilm Formation of Acneic Strains

—Protocol

Bacterial Strain and Bacterial Culture

The *Cutibacterium acnes* acneic strain ribotype 5 (RT5) HL043PA2/HM-514 and the *Cutibacterium acnes* non-acneic strain ribotype 6 (RT6) HL110PA3/HM-554 were obtained from BEI Resources American Type Culture Collection (Virginia, United States). These two strains belong to the phylotypes IA1 and II, respectively (McDowell, 2017). Bacteria, stored at −80° C., were initially plated on brain-heart infusion (BHI, BD) agar plates for RT6 strain and on reinforced clostridial medium (RCM) agar plates for RT5 strain, and were incubated under anoxic conditions at 37° C. using a BD GasPack™ System. Colonies were transferred into sterile conical 15-mL tubes (Falcon) containing 12 ml of RCM and after vortexing for homogenization, the falcon tube is completely filled with RCM medium and incubated for 72 h at 37° C.

Biofilms Formation on Glass Slide

In order to evaluate *Cutibacterium acnes* biofilm formation during exposition to the G2 dendrimer, 24-well culture plates with a flat glass bottom were used (Sensoplate, Greiner bio-one, Germany). The 72 h bacterial cultures (see paragraph above) were centrifuged at 7,500 g during 10 min at room temperature. The bacterial pellet was re-suspended in 5 ml of sterile physiologic water (SPW). Finally, 300 µl of bacterial inoculum ($OD_{580\ nm}$=0.8) were placed into the eight centre wells of 24-well culture plates. The plates were incubated 3 h in anaerobic condition to favour primary adhesion of the bacteria. After this incubation period, physiologic water was carefully removed in each well, and 1 ml of bacterial culture medium (RCM) supplemented or not with the G2-Dendrimer was added. The plates were incubated for 72 h at 37° C. in the anaerobic Whitley A85 Workstation.

After 72 h (biofilm formation), the RCM medium was carefully removed in each well in order to remove planktonic cells. Next, 300 µl of the SYTO 9 green fluorescent nucleic acid stain (Thermofisher) were added in each well and incubated 20 min in darkness condition. After that, the SYTO 9 stain was removed and 300 µl of SPW was added in each well. CLSM observations were immediately performed with a Zeiss LSM710 (Carl Zeiss Microscopy, Oberkochen, Germany) using a 63× oil immersion objective. Syto 9 was excited at 488 nm and fluorescence emission was detected from 500 to 550 nm. Images were taken every micrometer throughout the whole biofilm depth. For visualization and processing of three-dimensional (3D) image, the Zen 2.1 SP1 software (Carl Zeiss Microscopy, Oberkochen, Germany) was used. Quantitative analyses of images stacks were performed using the COMSTAT software (see Worldwide Website: imageanalysis.dk/) (Heydorn et al., 2000). Maximal and average biofilm thickness (µm) and their biomass volume ($µm^3/µm^2$) were determined. Each study was repeated a minimum of three times.

—Results

Figure 6A:
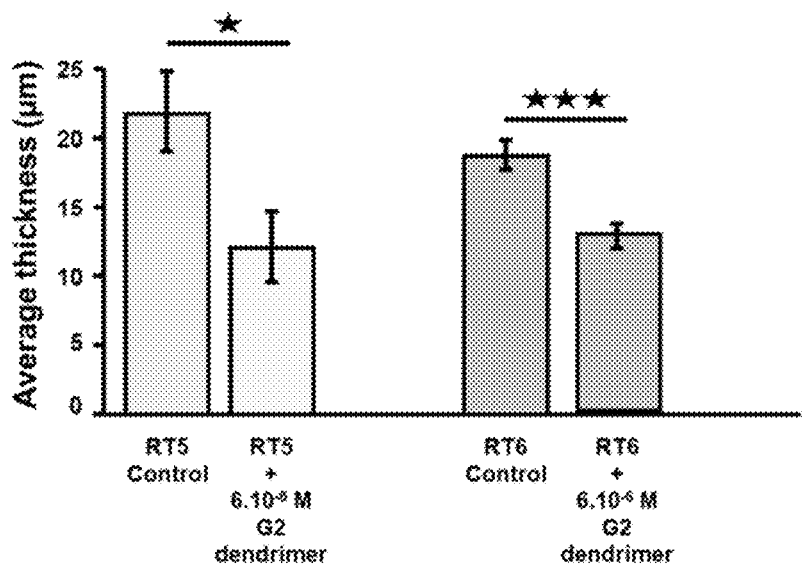
FIGS. 6A and 6B show the impact of the dendrimer of the invention on biofilm formed by non-acneic strain RT6 and that formed of acneic strain RT5. G2 dendrimer decreased the biofilm thickness for both strains. Of note, the G2 dendrimer significantly decreased the biomass density in the biofilm formed by RT5 strain while having no significant effect on the biomass density of the biofilm formed by RT6 strain.
Figure 6B:
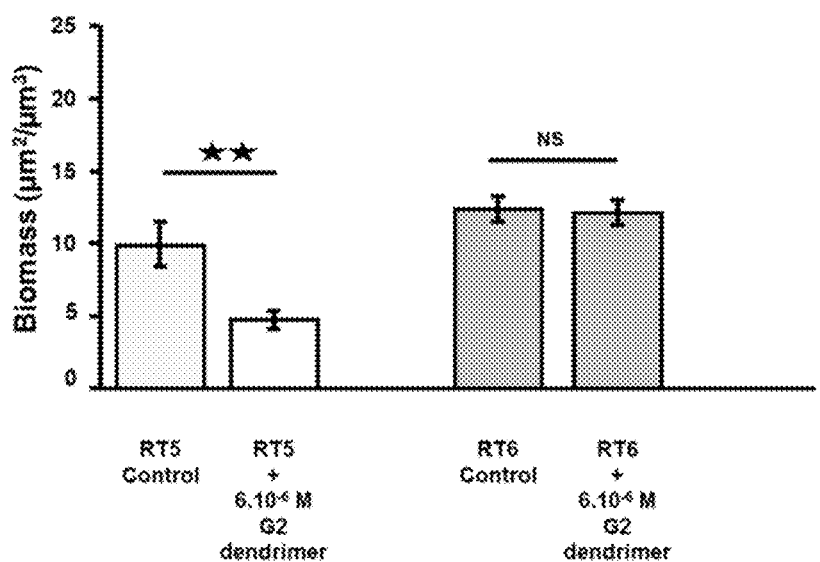
Figure 7:
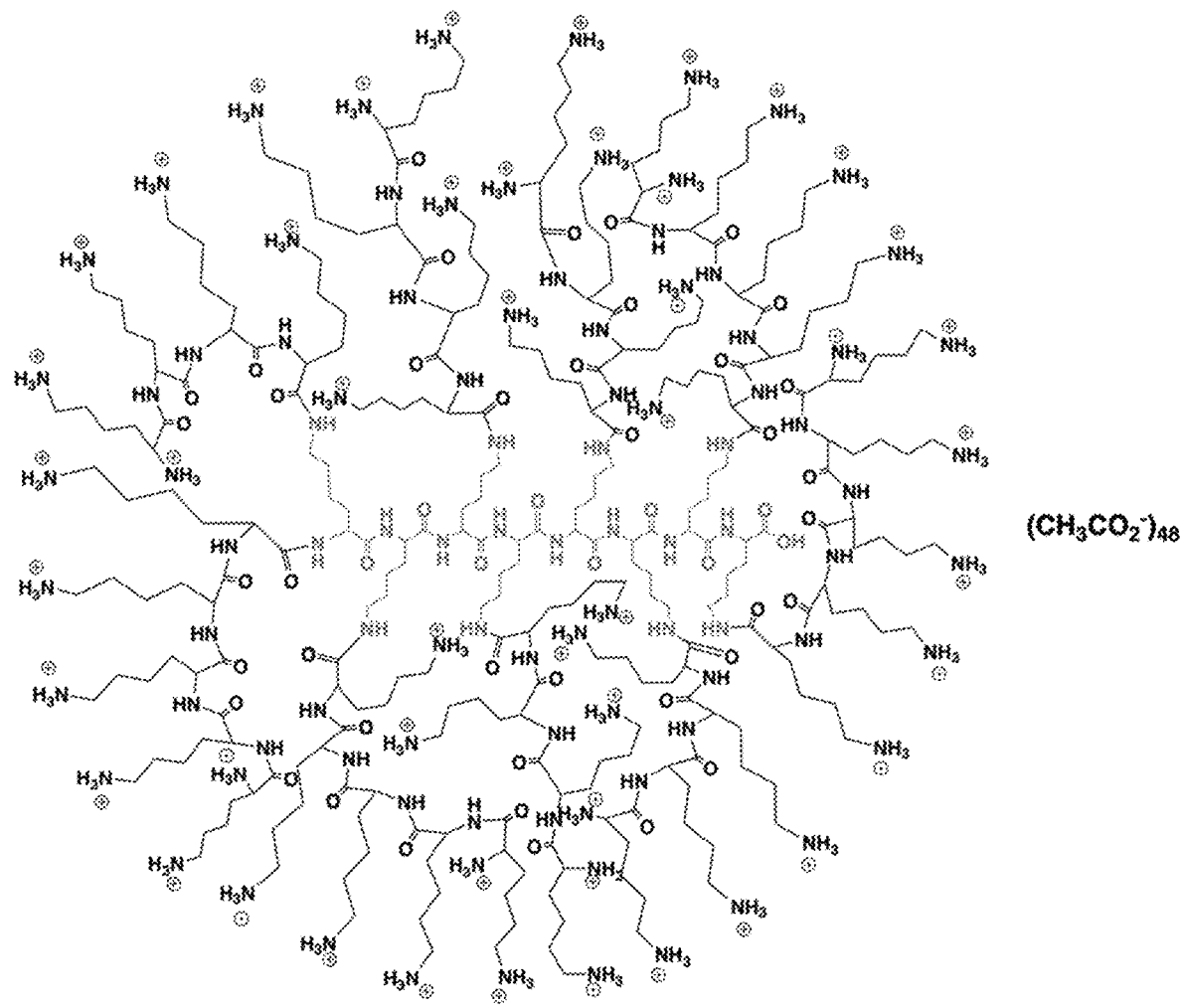
FIG. 7 shows an example of polylysine dendrimer of the invention.

The G2 dendrimer was shown to decrease the thickness of the biofilm for both RT5 (−48%) and RT6 (−32%) strains. Of note, the decrease in biofilm thickness was significantly more important for the acneic strain RT5 than for the non acneic strain RT6. Moreover, as shown in FIG. 6, the G2 dendrimer significantly decreased the biomass density in the biofilm for RT5 (−50%) while having no effect in the biomass density in the biofilm for RT6.

In conclusion, the polylysine dendrimer is expected to reduce the inflammatory response triggered by *C. acnes* biofilm whatever the strain, by reducing the thickness of biofilm while exerting a selective and specific inhibitory action on acneic strains by destabilizing their biofilm. This destabilization effect was not observed for the non-acneic strain RT6 as the biomass density remains unchanged.

Of note, such results are consistent with Example 6 which shows that the polylysine dendrimer increases the membrane fluidity in acneic RT5 strain, and not in non-acneic RT6 strain.

Example 8: Clinical Study

20 Caucasian subjects presenting greasy and prone to acne skin on face (50% of subjects between 14 and 25 years old and 50% of the subjects between 26 and 40 years old) applied on hemiface, twice a day, a cream containing 2 ppm of G2 Dendrimer (test cream) or a placebo cream for 28 days. The test formulation (G2 dendrimer formulation) was as follows:

| Commercial name | INCI name | % |
|---|---|---|
| Deionized water | Water | 88.00 |
| Dermofeel PA-3 | Sodium Phytate (and) Aqua (and) | 0.10 |
| Ecogel | Alcohol Lysolecithin (and) Sclerotium Gum (and) Xanthan Gum (and) Pullulan | 2.00 |
| SCB Jojoba oil | Simmondsia Chinensis Seed Oil | 3.00 |
| Dermofeel toco 70 non gmo | Tocopherol (and) Helianthus Annuus (Sunflower) Seed Oil | 0.10 |
| Lipex shea W | Shea Butter Cetyl Esters | 3.00 |
| Saboderm TTC | Caprylic/Capric Triglyceride | 3.00 |
| Dekaben C4 | Phenoxyethanol (and) Methylparaben (and) Ethylparaben (and) Butylparaben (and) Propylparaben | 0.80 |
| G2 Dendrimer | | 0.0002 |

G2 Dendrimer Significantly Improved the Aspect of Acneic Skin by Decreasing Acneic Lesions and Regulating Sebum Excretion Rate.

The placebo formulation was similar to that of the test formulation except that G2 dendrimer was replaced by water. The comedogenic potential and anti-imperfections effects are assessed after 28 days of use, in comparison with the number of lesions on the face before application (D0):

Clinical examination: The comedogenic potential and anti-imperfections effect of the test cream versus placebo was assessed after 28 days of use, in comparison with the number of lesions on the face before application (D0). On D0 and D28, the dermatologist examined the skin and counted global inflammatory lesions as well as papules and pustules on each hemi-face of each enrolled subject. The dermatologist also determined the number of global retentional lesions and blackheads on each hemi-face of each patient. The results are shown is FIGS. 5A, 5B and 5C.

Sebum level measurements: The quantity of sebum excreted to the skin surface was quantitatively evaluated with a COURAGE and KHAZAKA SM 810 PC Sebumeter® at day 28. The results are shown in FIG. 5D.

Figure 5A:
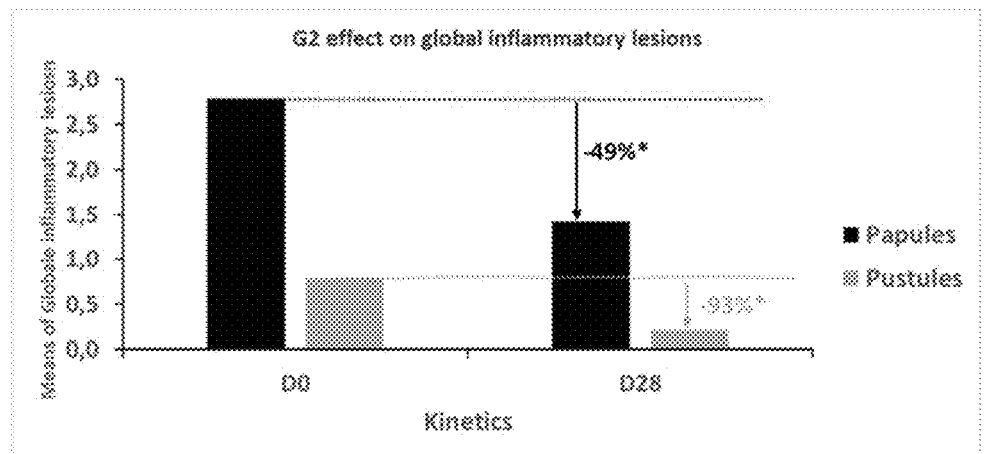
FIGS. 5A-5F show the results of the clinical study aiming at assessing the effect of a treatment with a test cream containing the G2 dendrimer (G2) versus placebo cream (placebo) on the number of inflammatory lesions (i.e. pustules and papules) (FIG. 5A), retentional lesions (i.e. blackheads and whiteheads) (FIG. 5B), and blackheads (FIG. 5C) as well as on sebum excretion rate (FIG. 5D) after 28 days of treatment.
Figure 5B:
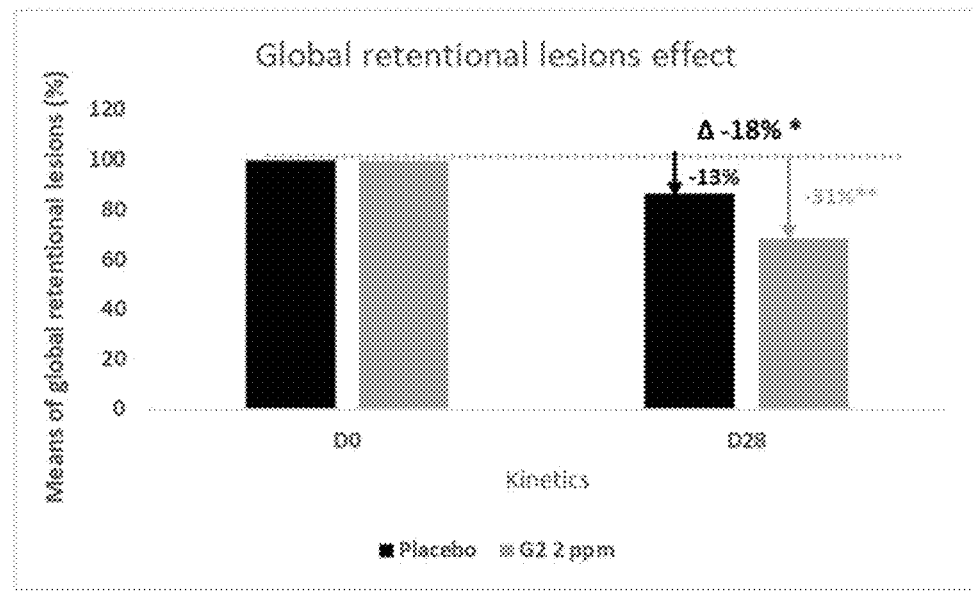
Figure 5C:
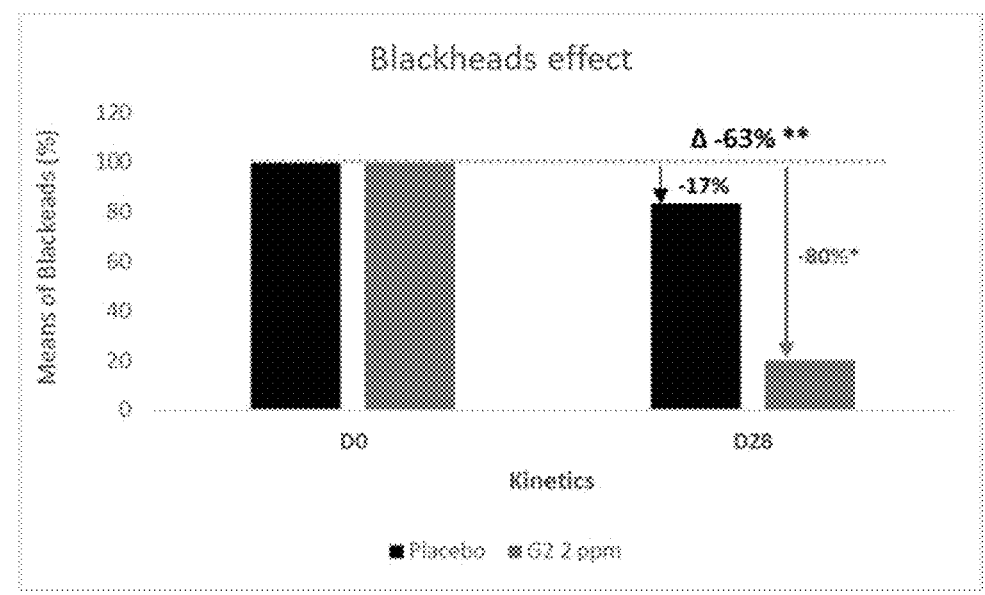
Figure 5D:
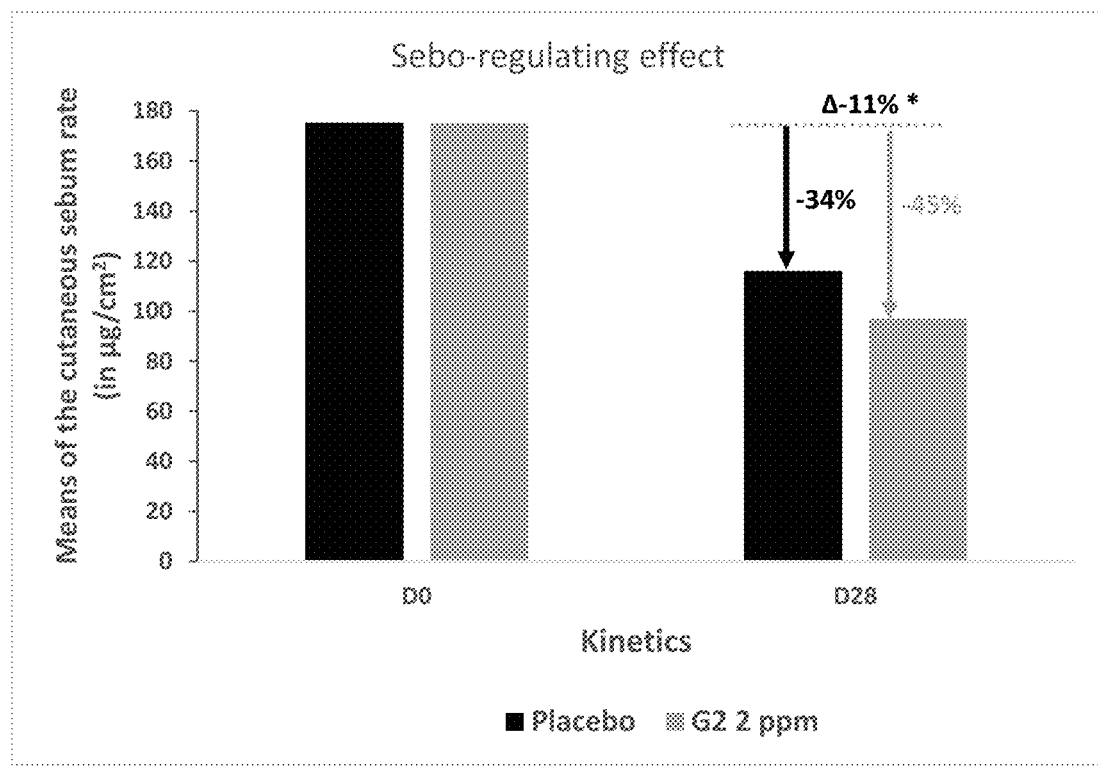

Results:

As illustrated in FIG. 5A-5C, the test cream comprising G2 dendrimer significantly decreased the number of blackheads, retentional lesions and inflammatory lesions after 28 days of treatment, as compared to the placebo cream. Moreover, the test cream also significantly decreased the rate of sebum excretion by the acneic skin as compared to the placebo cream (FIG. 5D). All together these data demonstrate that G2 dendrimer is an effective agent to manage acneic disorders.

*G2 Dendrimer Improves Microbiota of Acneic Skin

After 28 days of treatment, skin samplings (swabs) were performed on each hemifaces of each enrolled volunteers so as to quantify the *C. acnes* strains by metagenomic analysis and determine the effect of the test cream on *C. acnes* diversity versus placebo cream.

The principle of this metagenomics study is to amplify a region of *Cutibacterium acnes* and to sequence amplicons. Amplicons sequences are compared to SLST reference database (medbac.dk/slst/pacnes) that linked amplicons sequences to SLST types and clades and to phylotypes. This methodology is based on publication of Scholtz et al. (Scholz, 2014, supra) with modifications. SLST types and clades and phylotypes abundances and diversities were calculated for each sample and compared to evaluate treatment effect between groups made of volunteers treated with active formula and volunteers treated with placebo formula.

Protocol

Swabs were frozen and stored at −80° C. until DNA extraction. DNA extraction and purification were done using Qiagen DNeasy PowerSoil Kit (Cat #12888). Briefly, cells were lysed by the combination of mechanical (beads beating) and chemical (detergent) treatments. Extracted DNA was then purified on silica membrane.

Original *Cutibacterium acnes* SLST method (Scholz, 2014, supra), amplifies a region of 612 base pairs, that is too large to be sequenced using Illumina technology. New primers amplifying a region or 497 base pairs were designed, forward primer being place 74 nucleotides downstream original and reverse 26 nucleotides upstream. This modification will not allow distinction between SLST types A1 and A6 or SLST types E3 and E7. In both cases, these variants belong to same clades and phylotypes. DNA sequencing was performed on Illumina Miseq using paired-end technology. All sequences processing was performed using QIIME2 suite (qiime2.org/). After quality filtering, reads pairs were merged by overlapping, clustered and chimeric sequences were removed. SLST types were assigned to sequences against *Cutibacterium acnes* SLST reference database (medbac.dk/slst/pacnes) using 99% homology threshold.

Data Analysis.

Input Data

Raw data were normalized using the Total Sum Scaling (TSS) procedure, i.e. for a given sample, each SLST abundance is divided by the sum of all taxa abundances.

Abundance data were further filtered by removing SLST types observed in only one sample, before being statistically compared between groups.

Rarefaction

Rarefaction curves, f(sequences number)=SLST number, were drawn Past 3.20 software (palaeo-electronica.org/2001_1/past/issue1_01.htm). These curves allow to evaluate graphically whether sequencing depth is sufficient (when curves reach a plateau).

Alpha (α)-Diversity.

Shannon and Simpson diversity indices were calculated using Past 3.20 software. These two alpha-diversity measures were used to characterize the taxonomic diversity of each sample: the Shannon, entropy-like diversity and the Simpson (1-D) diversity. Both indices values depend on richness (number of different taxa) and equitability of populations, Simpson index being less affected by low abundant taxa. In both cases, index increases with diversity. Number of SLST (Richness) is presented, it can also be considered as a diversity metrics, with bias that same weight is given to high and low abundant SLST.

In all cases, SLST types normalized abundance data were used for calculation.

Abundances Comparison.

Strains types abundances at each level were compared using parametric paired Student T-test and non-parametric Wilcoxon Test and Sign Test. SLST types normalized and filtered abundance data were used for calculation.

Results

This study led to identify 32 SLST types among the tested samples, all related to Phylotypes described in the literature.

Phylotype IA1 was the most represented one, with SLST type A1 as major one, followed by Phylotypes II, IB, IA2, IC and III. This repartition was the same for samples treated with the test cream or the placebo cream. Phylotypes repartition varied depending on individual (age, gender) as well as sampling area. Phylotype IA1 was more abundant for most back samples compared to face samples. Our findings were consistent with the study of Dagnelie et al. (Dagnelie, 2018, supra) who further showed that phylotype IA1 was more abundant in acne skin than healthy one while phylotype II was described as less abundant on acneic skin than healthy one.

Figure 5E:
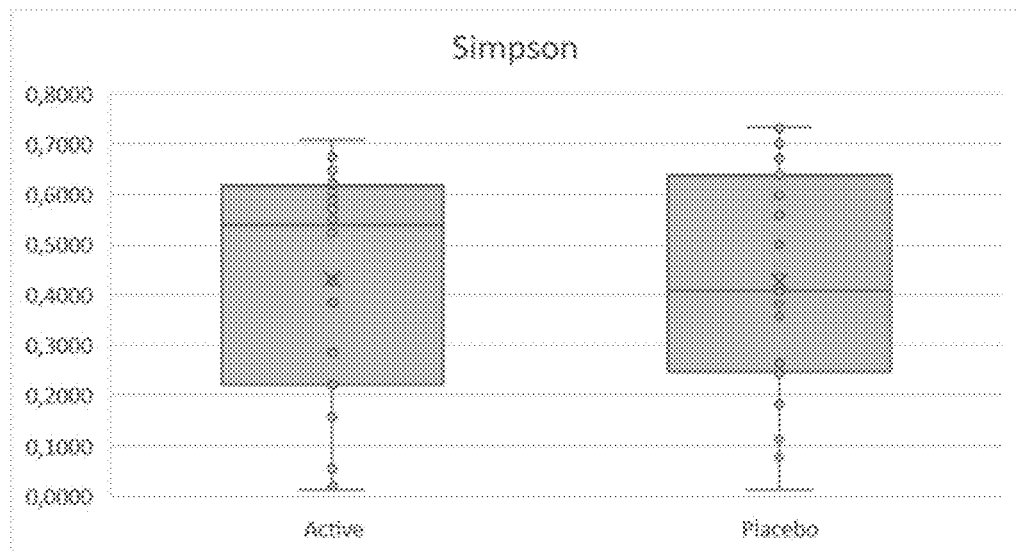
Figure 5F:
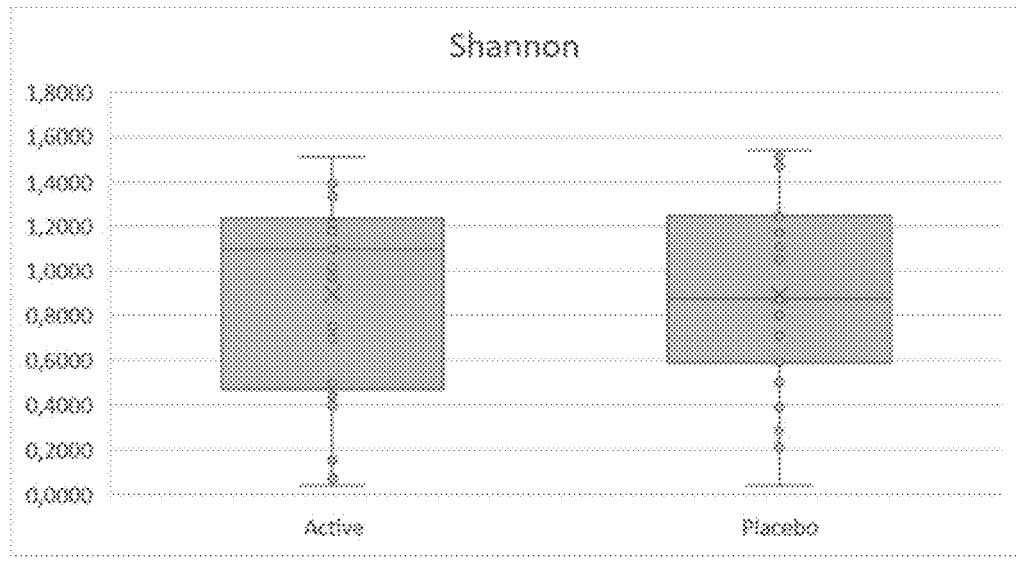

As shown in FIGS. 5E and 5F, treatment with the test cream increased strain diversity as compared to placebo cream after 28 days of treatment. We further note that the treatment with the test composition resulted in a decrease in acneic IA1 phylotype abundance and an increase in non-acneic phylotype II, as compared to placebo cream especially in male subjects and in subjects of at least 23 years old. G2 dendrimer thus exerts a beneficial action on C *acnes* population in acneic skin by limiting the acneic strains while promoting the non-acneic strains. In other words, G2 dendrimer can be used to rebalance *C. acnes* population in acneic and acne-prone skin.

The invention claimed is:

1. A method for managing a skin type selected from acneic skin, acne-prone skin and blemish-prone skin in a subject which comprises a step of topically administering an effective amount of a topical composition comprising an excipient and polylysine dendrimer or a salt thereof to said subject, wherein the polylysine dendrimer is an unconjugated poly-L-lysine second generation (G2) dendrigraft having an average degree of polymerization (DPn) from 40 to 60.

2. The method of claim 1, wherein the method restores or rebalances skin microbiota.

3. The method of claim 2, wherein the method decreases the abundance of a *C. acnes* strain selected from the group consisting of phylotypes IA1, IA2, IB and IC.

4. The method of claim 3, wherein the *C. acnes* strain is phylotype IA1.

5. The method of claim 2, wherein the method increases the abundance of a *C. acnes* strain of phylotype II or III.

6. The method of claim 5, wherein the *C. acnes* strain is phylotype II.

7. The method of claim 1, wherein the method:
improves skin aspect and feel;
restores skin comfort;
improves or treats blemishes;
soothes skin;
decreases skin redness or skin inflammation;
decreases skin sebum secretion;
decreases visible lesions;
improves skin desquamation; or combinations thereof.

8. The method of claim 1, wherein the polylysine dendrimer comprises a linear poly-L-lysine core containing an ε-amino group, and wherein the ε-amino group is substituted with a poly-L-lysine moiety.

9. The method of claim 8, wherein the linear poly-L-lysine core contains from 6 to 10-lysine residues, and wherein the poly-L-lysine moiety contains from 2 to 6 lysine residues.

10. The method of claim 1, wherein the polylysine dendrimer is a polycationic dendrimer, and wherein the polycationic dendrimer is used with a counter anion of acetate.

11. The method of claim 1, wherein the topical composition comprises:
from 0.1 to 100 ppm of the polylysine dendrimer;
from 0% to 20% by weight of one or more additional active agents; and
from 70% to 99.9999% by weight of one or more excipients.

12. The method of claim 1, wherein the topical composition comprises from 0.1 to 20 ppm of the polylysine dendrimer.

13. The method of claim 1, wherein the topical composition comprises from 0.5 to 10 ppm of the polylysine dendrimer.

14. The method of claim 1, wherein the topical composition comprises from 0.5 to 7 ppm of the polylysine dendrimer.

* * * * *